(12) United States Patent
Hirata

(10) Patent No.: US 8,043,211 B2
(45) Date of Patent: Oct. 25, 2011

(54) ENDOSCOPE DEVICE WITH A HEAT REMOVAL PORTION

(75) Inventor: Yasuo Hirata, Tokyo (JP)

(73) Assignee: Olympus Corporation (JP)

( * ) Notice: Subject to any disclaimer, the term of this patent is extended or adjusted under 35 U.S.C. 154(b) by 1112 days.

(21) Appl. No.: 11/738,840

(22) Filed: Apr. 23, 2007

(65) Prior Publication Data

US 2007/0191684 A1    Aug. 16, 2007

Related U.S. Application Data

(63) Continuation of application No. PCT/JP2005/019600, filed on Oct. 25, 2005.

(30) Foreign Application Priority Data

Oct. 25, 2004    (JP) ............................. P2004-309281

(51) Int. Cl.
*A61B 1/06* (2006.01)
(52) U.S. Cl. ...................................... 600/179; 600/175
(58) Field of Classification Search .................. 600/178, 600/179, 175, 152, 129
See application file for complete search history.

(56) References Cited

U.S. PATENT DOCUMENTS

| | | | |
|---|---|---|---|
| 6,796,939 B1 * | 9/2004 | Hirata et al. ................. | 600/179 |
| 2005/0137459 A1 * | 6/2005 | Chin et al. ................... | 600/179 |
| 2005/0177027 A1 * | 8/2005 | Hirata .......................... | 600/179 |
| 2005/0197536 A1 * | 9/2005 | Banik et al. .................. | 600/179 |
| 2006/0058584 A1 * | 3/2006 | Hirata .......................... | 600/179 |
| 2006/0063976 A1 * | 3/2006 | Aizenfeld et al. ............ | 600/179 |
| 2006/0069309 A1 * | 3/2006 | Ono .............................. | 600/134 |
| 2006/0116553 A1 * | 6/2006 | Dunki-Jacobs et al. ...... | 600/179 |
| 2006/0171693 A1 * | 8/2006 | Todd et al. ....................... | 396/17 |

FOREIGN PATENT DOCUMENTS

| | | |
|---|---|---|
| JP | 11-267099 | 10/1999 |
| JP | 2001-078175 | 3/2001 |
| JP | 2002-562 | 1/2002 |
| JP | 2002-000562 | 1/2002 |
| JP | 2004-248835 | 9/2004 |
| JP | 2005-027851 | 2/2005 |
| JP | 2005-27851 | 2/2005 |
| JP | 2005-110879 | 4/2005 |

OTHER PUBLICATIONS

English translation of International Search Report dated Jan. 31, 2006 issued in connection with corresponding PCT application No. PCT/JP2005/019600.
English translation of Written Opinion dated Jan. 31, 2006 issued in connection with corresponding PCT application No. PCT/JP2005/019600.

* cited by examiner

*Primary Examiner* — John P Leubecker
(74) *Attorney, Agent, or Firm* — Ostrolenk Faber LLP

(57) ABSTRACT

This endoscope device includes: an LED adaptor that has a plurality of LED chips and that can be removably fitted onto a distal end of an insertion portion that is inserted into a body cavity of an endoscopy subject; an LED supporting block that is provided on the LED adaptor and that supports the plurality of LED chips; and a heat removal portion that removes heat from the LED supporting block.

10 Claims, 23 Drawing Sheets

US 8,043,211 B2

ENDOSCOPE DEVICE WITH A HEAT REMOVAL PORTION

CLAIM OF PRIORITY

This application is continuation application of a PCT Application No. PCT/JP2005/019600, filed on Oct. 25, 2005, whose priority is claimed on Japanese Patent Application No. 2004-309281, filed Oct. 25, 2004, the contents of which are incorporated herein by reference.

BACKGROUND OF THE INVENTION

1. Technical Field

The present invention relates to an endoscope device having an LED adaptor that has an LED-based illumination device and can be fitted onto a distal end of an insertion portion that is inserted into the lumen of an endoscopy subject.

2. Background Art of the Invention

In endoscope devices that are used in medicine and industry, an objective lens group that is used for observation or for image pickup, and an illumination device that is used to light up the area around an endoscopy subject inside a body cavity are provided at a distal end side of an insertion portion that is inserted into the body cavity. A device that irradiates light from an external light source onto a subject via an optical fiber is widely used for the illumination device. In recent years, devices have been developed in which light emitting diodes (referred to in this specification as LED) are mounted on the distal end of the insertion portion, and the area around the endoscopy subject is lit by light from these LED (for example, refer to Japanese Unexamined Patent Application, First Publication No. 2002-562).

SUMMARY OF THE INVENTION

The endoscope device of the present invention includes: an LED adaptor that has a plurality of LED chips and that can be removably fitted onto a distal end of an insertion portion that is inserted into a body cavity of an endoscopy subject; an LED supporting block that is provided on the LED adaptor and that supports the plurality of LED chips; and a heat removal portion that removes heat from the LED supporting block.

In the endoscope device of the present invention, it is also possible for the heat removal portion to transmit the heat from the LED supporting block to another place, and it is also possible for the heat removal portion to cool the LED supporting block.

In the endoscope device of the present invention, it is also possible for the heat removal portion to be provided with a first heat discharge component that has one end that is connected to the LED supporting block and has another end that extends as far as a rear end surface of the LED adaptor, and when the LED adaptor is mounted on the insertion portion, for the other end of the first heat discharge component to be in contact with a distal end surface of the insertion portion.

In the endoscope device of the present invention, it is also possible for the heat removal portion to be provided with: a connecting plug that is provided at the distal end of the insertion portion and is in contact with the first heat discharge component: and with a second heat discharge component that is provided inside the insertion portion and that has one end that is connected to the connecting plug and has another end that extends to a proximal end side of the insertion portion, and when the LED adaptor is mounted on the insertion portion, for the other end of the first heat discharge component to be in contact with the connecting plug.

In the endoscope device of the present invention, it is also possible for the heat removal portion to be further provided with a heat transmitting portion that is provided between the connecting plug and the second heat discharge component.

In the endoscope device of the present invention, it is also possible for the heat removal portion to be further provided with a heat transmitting portion that is provided on an outer circumferential surface of the LED adaptor.

In the endoscope device of the present invention, it is also possible for the heat removal portion to be further provided with a heat transmitting portion that is provided between the LED chips and the LED supporting block, or between the LED supporting block and the first heat discharge component.

In the endoscope device of the present invention, it is also possible for the heat removal portion to be further provided with a heat transmitting portion that is provided on an outer circumferential surface of the LED supporting block.

In the endoscope device of the present invention, it is also possible for the heat transmitting portion to be a Peltier element.

In the endoscope device of the present invention, it is also possible for a bending portion that is able to perform a bending operation in an optional direction to be provided in the distal end portion, and for the bending portion to be formed by a columnar elastic component having a plurality of pressure chambers that are aligned in a circumferential direction, and for the bending portion to perform a bending operation as a result of highly pressurized air being selectively supplied to or discharged from the plurality of pressure chambers of the columnar elastic material, and for the columnar elastic component to be formed in a circular cylinder shape, and for a highly thermoconductive internal coil that regulates displacement towards an inner side in a radial direction to be placed on an inner circumferential side of the columnar elastic component that is formed in a circular cylinder shape, and for the other end of the second heat discharge component to be connected to the internal coil.

In the endoscope device of the present invention, it is also possible for the LED adaptor to be provided with: an exterior packaging component; and a thermoconductive component that is provided on an inner side of the exterior packaging component and is more highly thermoconductive than the exterior packaging component. It is also possible for the thermoconductive component to be in contact with the LED chips and the distal end surface of the insertion portion.

In the endoscope device of the present invention, it is also possible for the thermoconductive component to have either a linear shape, a block shape, or a cylindrical shape. It is also possible for the thermoconductive component to be formed from any one of a metal such as aluminum or copper, a ceramic such as aluminum nitride, or a resin such as silicon rubber or acrylic rubber.

DESCRIPTION OF THE PREFERRED EMBODIMENTS

Next, each of the embodiments of the present invention will be described based on the drawings. Note that in the descriptions of the respective embodiments, the same descriptive symbols are used for identical components in duplicated portions and a description thereof is partially omitted.

Firstly, the first embodiment shown in FIGS. 1 to 10 will be described.

Figure 2:
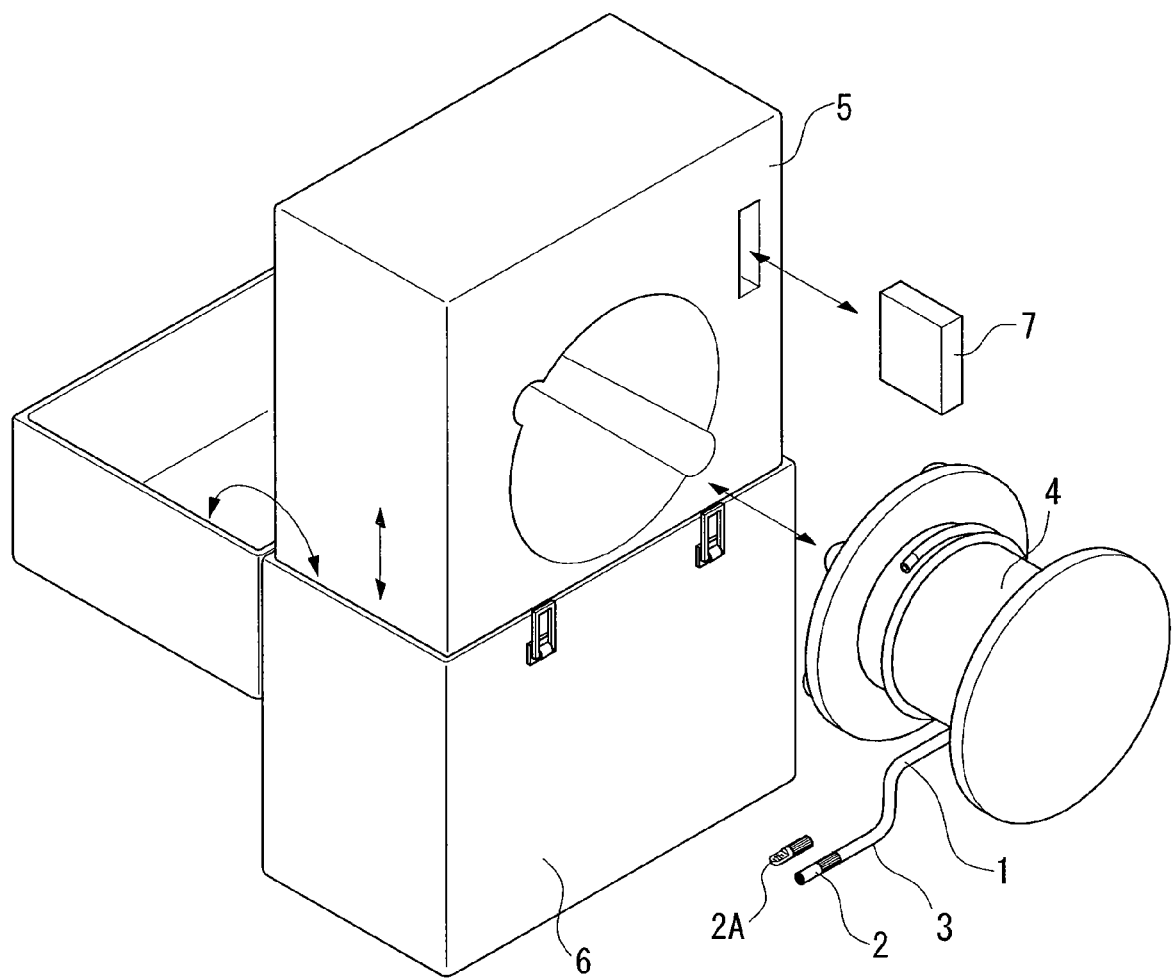
FIG. 2 is a perspective view showing a state in which the endoscope device of the first embodiment has been disassembled.
Figure 3:
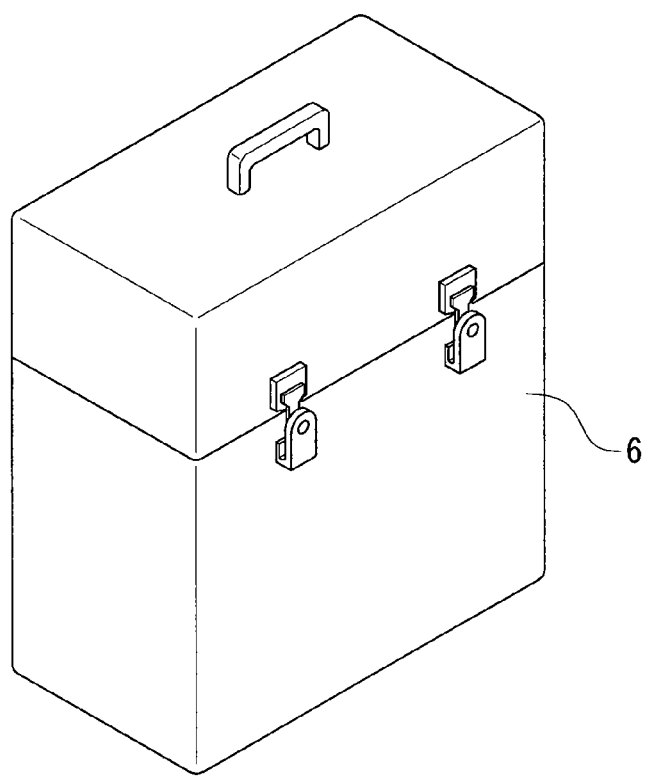
FIG. 3 is a perspective view showing a state in which the endoscope device of the first embodiment has been assembled and housed in a case.
Figure 4:
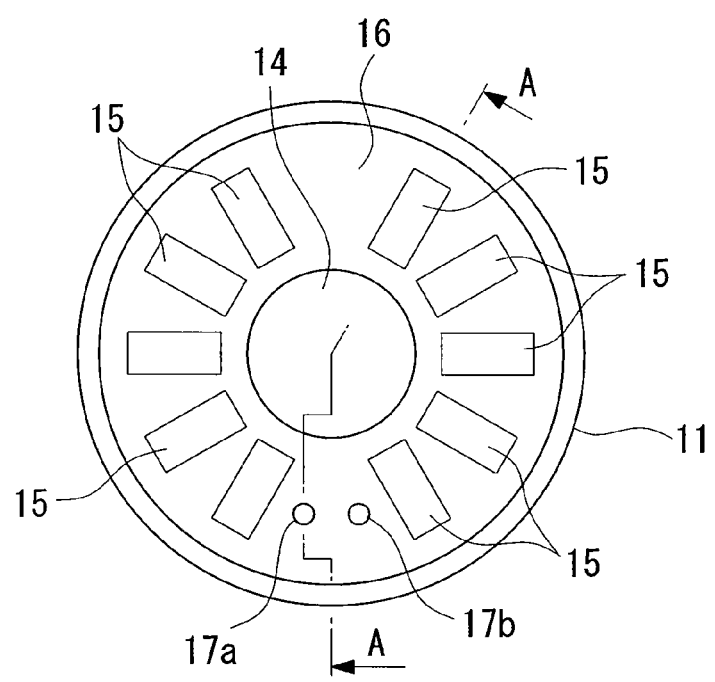
FIG. 4 is a front view showing an LED adaptor provided in the endoscope device of the first embodiment.
Figure 5:
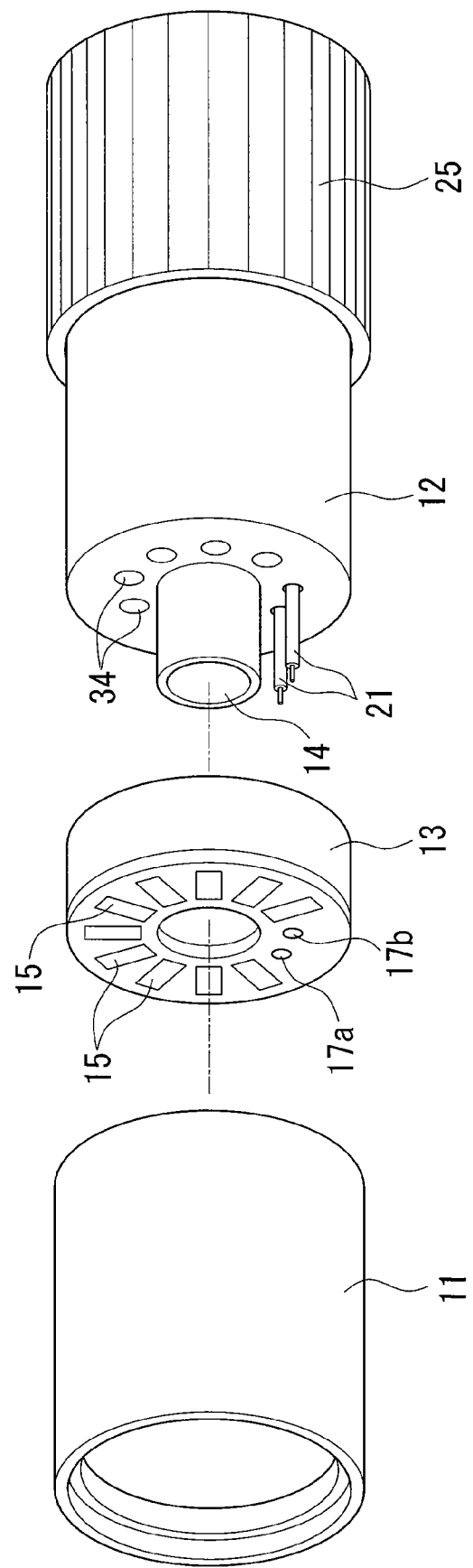
FIG. 5 is an exploded perspective view showing the LED adaptor provided in the endoscope device of the first embodiment.
Figure 6:
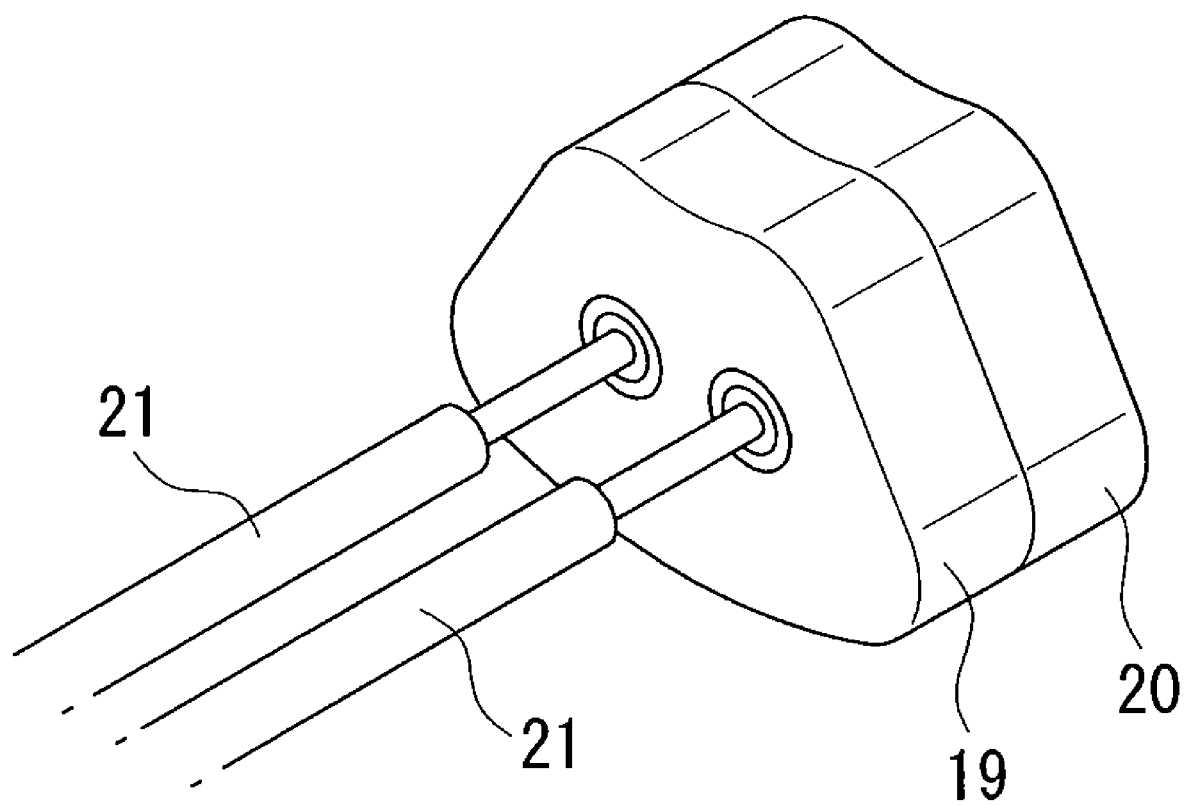
FIG. 6 is a perspective view showing a state in which an electrode substrate and conductive rubber that are provided in the endoscope device of the first embodiment are superimposed.

An overall schematic structure of an endoscope device of the present invention is shown in FIGS. 2 and 3. As is shown in FIGS. 2 and 3, this endoscope device is provided with an elongated insertion portion 1 that is inserted into a body cavity of an endoscopy subject, and a box-shaped device main body 5 from which the insertion portion 1 can be withdrawn. The insertion portion 1 is wound onto a drum 4 and the drum 4 is rotatably housed in the device main body 5. As is shown in FIG. 2 and FIG. 3, the device main body 5 housing the drum 4 is stored inside a storage case 6 used for carrying the endoscope device. The insertion portion 1 is almost entirely formed by a flexible tube, and a bending portion 3 that is capable of being bent in a desired direction by remote operation from the device main body 5 is provided in the vicinity of a distal end portion of the insertion portion 1. In addition, an LED adaptor 2 that is provided with an LED-based illumination device is removably fitted onto the distal end of the insertion portion 1. Note that, as is shown in FIG. 2, a replacement LED adaptor 2A is prepared for the endoscope device. This replacement LED adaptor 2A is stored in a storage pocket 7 that is provided in the device body unit 5.

A CCD 90 (see FIG. 1) is provided as an image pickup device at a distal end of the insertion portion 1 of this endoscope device. Image signals captured by this CCD 90 pass along a signal wire inside the insertion portion 1 and are output to a signal processing circuit (not shown) that is incorporated in the device main body 5. Signals that have been processed by this signal processing circuit are then projected as video images on an image display unit such a liquid crystal panel or the like. Note that, in addition to the signal processing circuit, a main power supply circuit (not shown) that is connected to a battery power supply and the like are also incorporated in the device main body 5.

Figure 1:
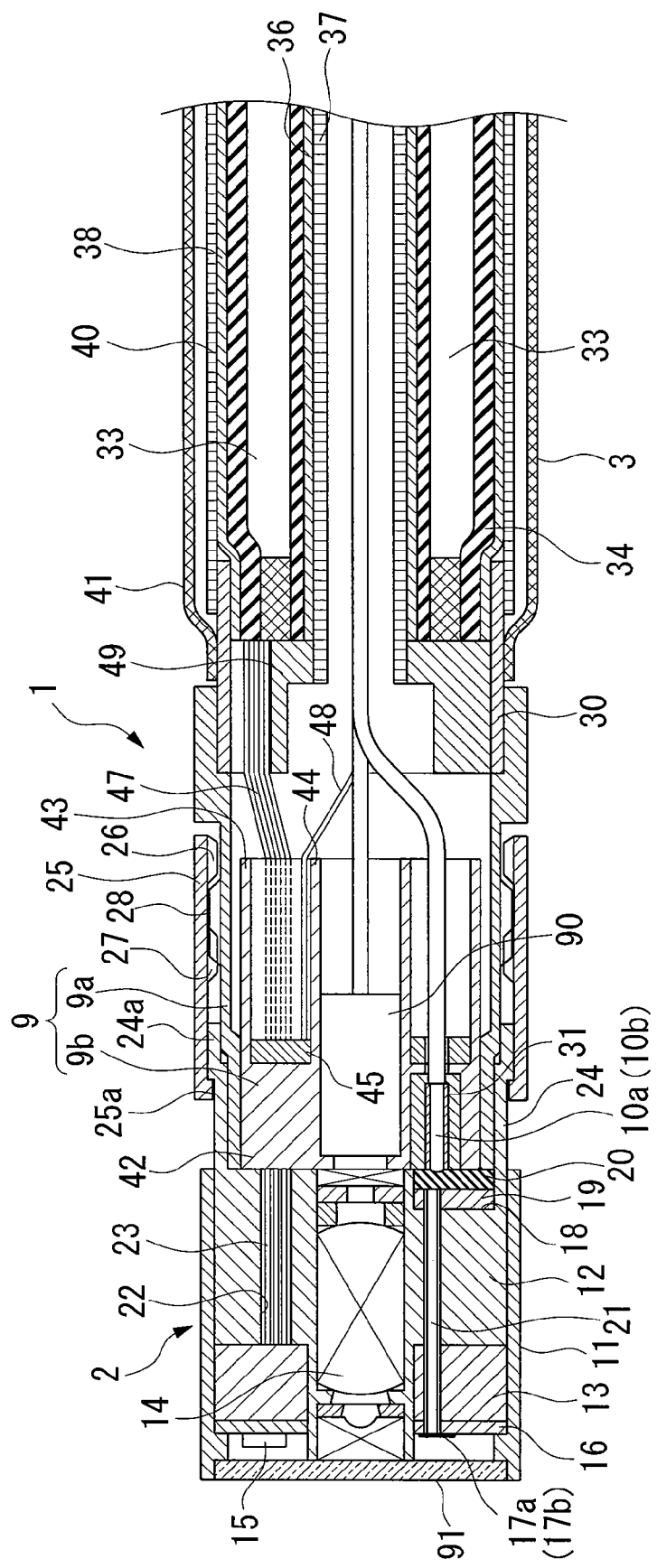
FIG. 1 is a longitudinal cross-sectional view of an endoscope device of a first embodiment of the present invention, and shows a state in which an LED adaptor is mounted on a distal end of an insertion portion (corresponding to a cross section A-A in FIG. 4).
Figure 10:
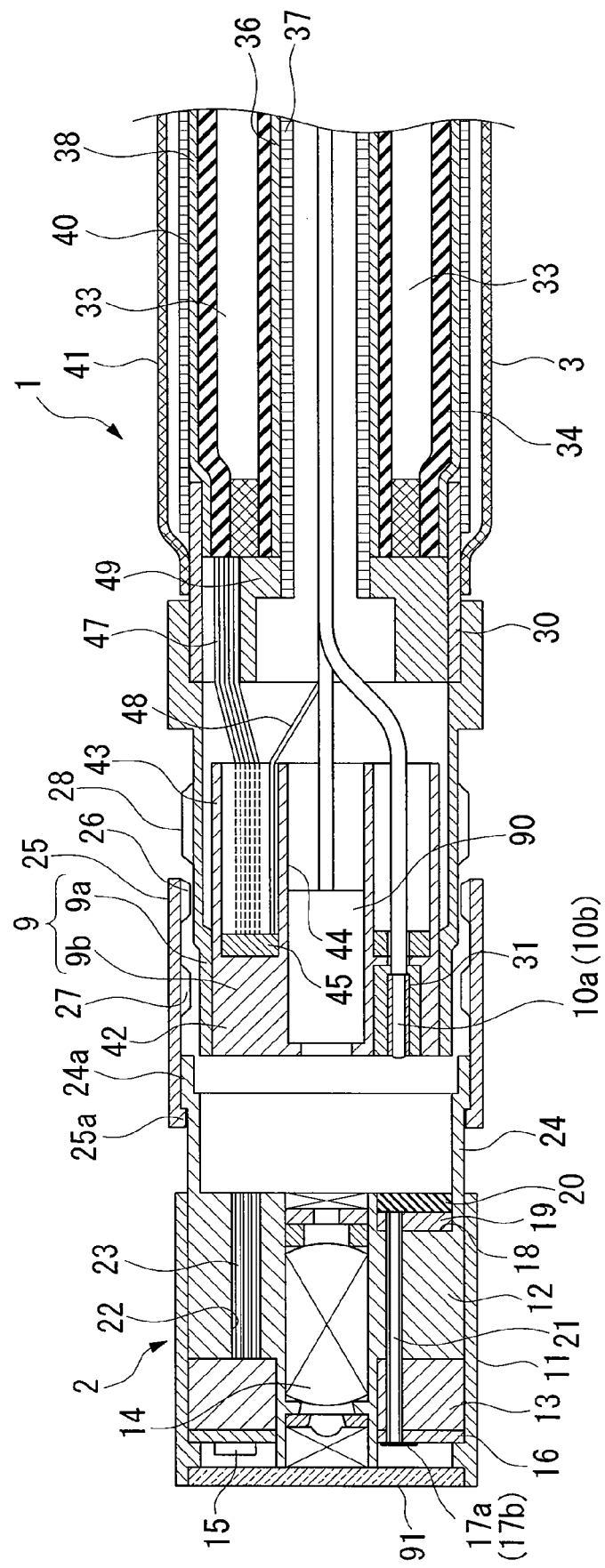
FIG. 10 is a longitudinal cross-sectional view of an endoscope device of the first embodiment of the present invention, and shows a state prior to an LED adaptor being mounted on a distal end of an insertion portion (corresponding to the cross section A-A in FIG. 4).

As is shown in FIGS. 1 and 10, a connecting plug 9 that is formed by a metal outer cylinder 9a and a CCD holder 9b is provided at a distal end of the insertion portion 1. A front connector 30 of the bending portion 3 (described below) is connected to a rear end portion of the outer cylinder 9a. The CCD 90 described above is mounted on an axial center portion of the CCD holder 9b. A pair of electrodes 10a and 10b that supply current to the lens adaptor 2 side are mounted via a non-conductive component 31 on a front end surface of the CCD holder 9b. The CCD holder 9b is formed from a metal such as aluminum or copper that is highly thermoconductive, or from a ceramic material such as aluminum nitride, and is fitted onto and fixed to an inner circumferential portion of the outer cylinder 9a.

As is shown in FIGS. 1, 4, 5, and 10, a lens supporting block 12 and an LED supporting block 13 are housed inside a substantially circular cylinder-shaped adaptor housing 11 of the lens adaptor 2. Overall, the lens supporting block 12 is formed substantially in a thick circular cylinder shape, and an objective lens group 14 that is used to link together images of an endoscopy subject on the CCD 90 is mounted in an inner circumferential portion thereof. The LED supporting block 13 is formed as a circular plate having a hole therein and having the same outer diameter as the lens supporting block 12. A plurality of LED chips 15 are mounted on a front surface side of the LED supporting block 13 via a thin non-conductive plate-shaped component 16. The LED supporting block 13 is formed from a metal such as aluminum or copper that is highly thermoconductive, or from a ceramic material such as aluminum nitride, and is bonded onto a front surface of the lens supporting block 12.

Boundary faces of the non-conductive plate-shaped component 16, the LED supporting block 13, and the lens supporting block 12 may also be bonded by an adhesive agent having excellent thermal conductivity (for example, silicon).

Moreover, the non-conductive plate-shaped component 16 is formed having substantially the same shape as the front surface of the LED supporting block 13, and a pair of electrodes 17a and 17b as well as the plurality of LED chips 15 are embedded in the non-conductive plate-shaped component 16 such that their front surfaces are exposed towards the front. On the front surface side of the non-conductive plate-shaped component 16, the pair of electrodes 17a and 17b are joined by wire bonding to the plurality of LED chips 15. Sealing glass 91 that covers the front of the LED chips 15 is installed on a front end portion of the adaptor housing 11.

A substantially fan-shaped recessed portion 18 is provided in a rear surface of the lens supporting block 12, and an electrode substrate 19 as well as conductive rubber 20 are housed in a superimposed state in the recessed portion 18. The electrode substrate 19 is superimposed on the front surface side of the conductive rubber 20, and a pair of electrode terminals (not shown) on a rear surface side of the conductive rubber 20 are in contact with the conductive rubber 20. A wire 21 is connected to each electrode terminal, and the respective wires 21 pass through the lens supporting block 12 and the LED supporting block 13 and are connected to the respective electrodes 17a and 17b.

The conductive rubber 20 has a non-conductive rubber material such as silicon rubber, and conductive components such as nickel particles or gold plated metal particles are embedded in a dotted pattern in this silicon rubber. The conductive rubber 20 is generally known as a dot type of anisotropic conductive rubber. Because the conductive rubber 20 has the above described structure, if the rubber material, which is an elastic object, is pressed in the thickness direction thereof, the conductivity between conductive components whose density has been increased by the resulting compression deformation increases so that conductivity in the thickness direction is allowed. However, because the rubber material is a non-conductive component, a non-conductive state is maintained in directions other than the thickness direction (for example, the circumferential direction) of the rubber material. When the lens adaptor 2 is connected to the insertion portion 1, the conductive rubber 20 is pressed from the rear surface side thereof by the electrodes 10a and 10b of the connecting plug 9. As a result, the electrodes 10a and 10b of the connecting plug 9 and the electrode terminals on the electrode substrate 19 that face these become mutually conductive.

As is shown in FIG. 1 and FIG. 10, a plurality of through holes 22 that penetrate in an axial direction are provided in the lens supporting block 12. Heat discharge wires (i.e., first heat discharging components) 23 that are formed from a highly thermoconductive metal such as copper are inserted into each of the through holes 22. The heat discharge wires 23 of the present embodiment may be wires formed by bundling together a plurality of metal wires or may be formed by a single metal rod material. A highly thermoconductive ceramic rod material (for example, aluminum nitride) may also be used. One end of the metal wires is connected by pressure welding to the rear surface of the LED supporting block 13, while the other end is uncovered at the rear surface of the lens supporting block 12 and is placed against a distal end surface of the connecting plug 9 (i.e., the CCD plug 9b) when the LED adapter 2 is connected to the insertion portion 1. Note that the heat discharge component 23 may be a single metal wire or may be a plurality of metal wires. Moreover, when a connection between the heat discharge components 23 and the LED adapter 2 of the present invention is referred to, this does not mean a mutual bonding of components by welding or the like, but simply means a thermoconductive connection including such as when the components are touching each other.

A cylindrical wall 24 that has a step-shaped enlarged diameter portion 24a extends upright from a rear end portion of the lens supporting block 12, and a connecting ring 25 that can be displaced in an axial direction and a rotational direction is externally fitted onto the cylindrical wall 24. An inward facing flange 25a is formed integrally with one end portion of the connecting ring 25, and displacement of the connecting ring 25 in the axial direction is restricted by this inward facing flange 25a and the enlarged diameter portion 24a of the cylindrical wall 24. In addition, a first female thread 26 and a second female thread 27 are provided a predetermined distance apart in the axial direction on an inner circumferential surface of the connecting ring 25.

In contrast, a male thread 28 used for fixing is formed on an outer circumferential surface of the outer cylinder 9a of the connecting plug 9. By screwing the first female thread 26 and the second female thread 27 of the connecting ring 25 in sequence onto the male thread 28, the LED adaptor 2 can be connected to the connecting plug 9. Namely, if the connecting ring 25 of the LED adaptor 2 is screwed onto the front end portion of the connecting plug 9 and if, in this state, the connecting ring 25 is rotated in a predetermined direction, then any displacement in the axial direction of the connecting ring 25 is restricted by the inward facing flange 25a abutting against the enlarged diameter portion 24a of the cylindrical wall 24. The male thread 28 of the connecting plug 9 is then fastened into the first female thread 26 and is then fastened onto the second female thread 27. The electrodes 10a and 10b are then made to press against the conductive rubber 20 so that the connecting plug 9 and the LED adapter 2 become connected. Note that, after the male thread 28 of the connecting plug 9 has been screwed into the second female thread 27, the engagement of the first female thread 26 with the male thread 28 is undone, however, the first female thread 26 functions as a stopper to prevent the connecting plug 9 falling out in the unlikely event that the engagement becomes undone between the male thread 28 and the second female thread 27.

Figure 9:
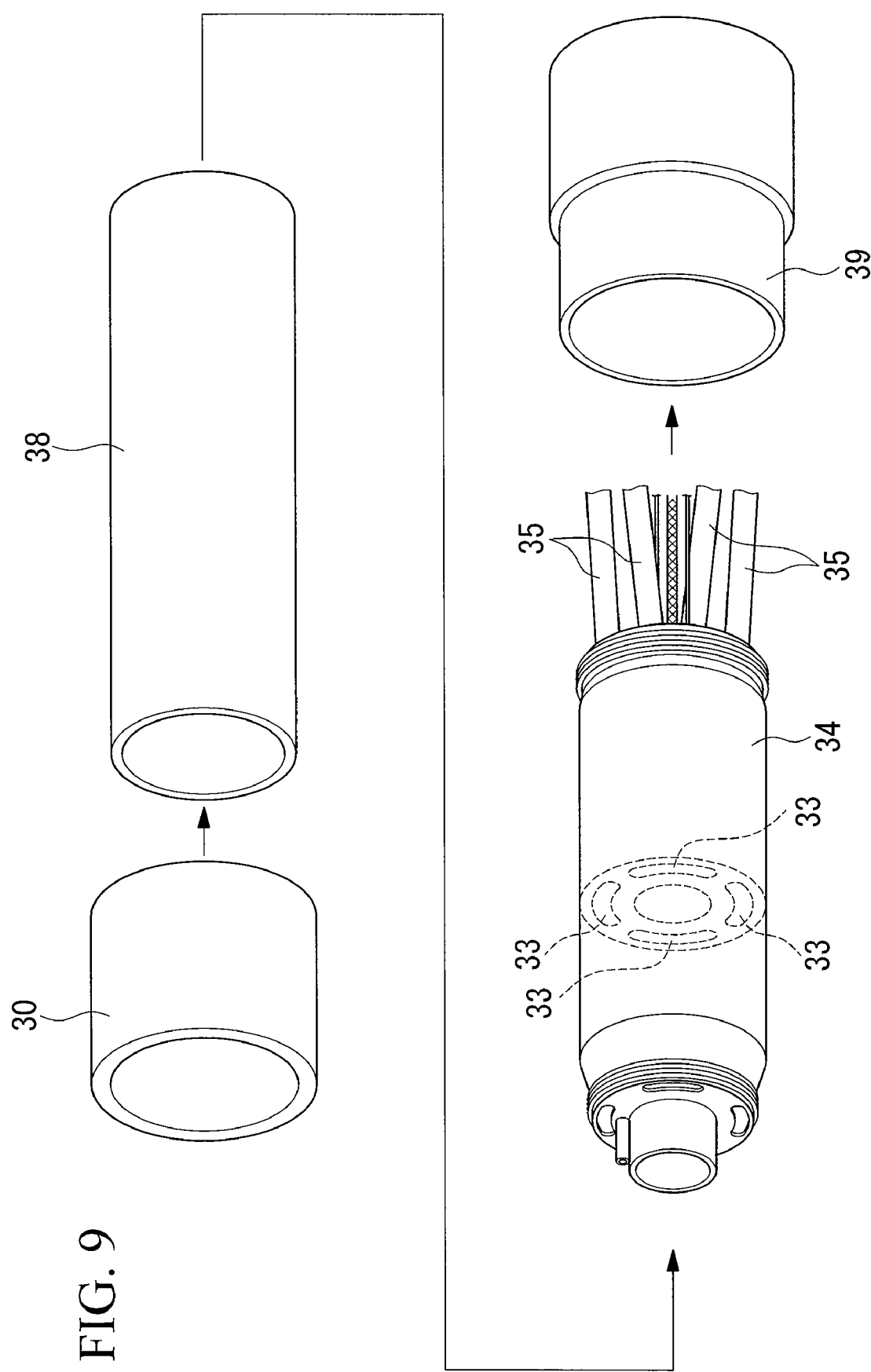
FIG. 9 is an exploded perspective view showing a bending portion provided in the endoscope device of the first embodiment.

As is shown in FIG. 1, FIG. 9, and FIG. 10, the main constituent element of the bending portion 3 is a columnar elastic component 34 in which four pressure chambers 33 are formed in a circumferential direction. Distribution tubes 35 are connected to each pressure chamber 33 of the columnar elastic component 34. Each distribution tubes 35 is connected to an air supply and discharge apparatus (not shown) that is able to switch between supplying and discharging air using an electromagnetic valve. The columnar elastic component 34 is formed from silicon resin or the like, and has an overall shape of a substantially circular cylinder.

An internal tube 36 that is formed from a flexible material and an internal coil 37 are packaged inside an inner circumferential portion of the columnar elastic component 34. The internal coil 37 is formed from a highly thermoconductive metal such as brass or copper and is able to be deformed in an axial direction and a bending direction. An external tube 38 that is formed from a flexible material is fitted onto an outer circumferential portion of the columnar elastic component 34. Note that the vicinities of both end portions of the internal tube 36 and the external tube 38 are fixed to the columnar elastic component 34.

The front connector 30 is joined to a front edge portion of the external tube 38, and a rear connector 39 is joined to a rear edge portion thereof. As is described above, the front connector 30 is connected to a rear end portion of the outer cylinder 9a of the connecting plug 9, while the rear connector 39 is connected to a flexible tube (not shown) on a proximal end side of the insertion portion 1. In addition, a metal external coil 40 that is able to be deformed in an axial direction and a bending direction is fitted so as to span across outer circumferential surfaces of the front connector 30 and the rear connector 39 that are mutually connected via the external tube 38. This external coil 40 and the above described internal coil 36 restrict expansion deformation in the radial direction of the elastic component 34 while allowing bending deformation of the columnar elastic component 34. A protective mesh 41 that surrounds the outer side of the external coil 40 at a predetermined distance is mounted on an outer circumferential surface of the front connector 30 and the rear connector 39.

Figure 7:
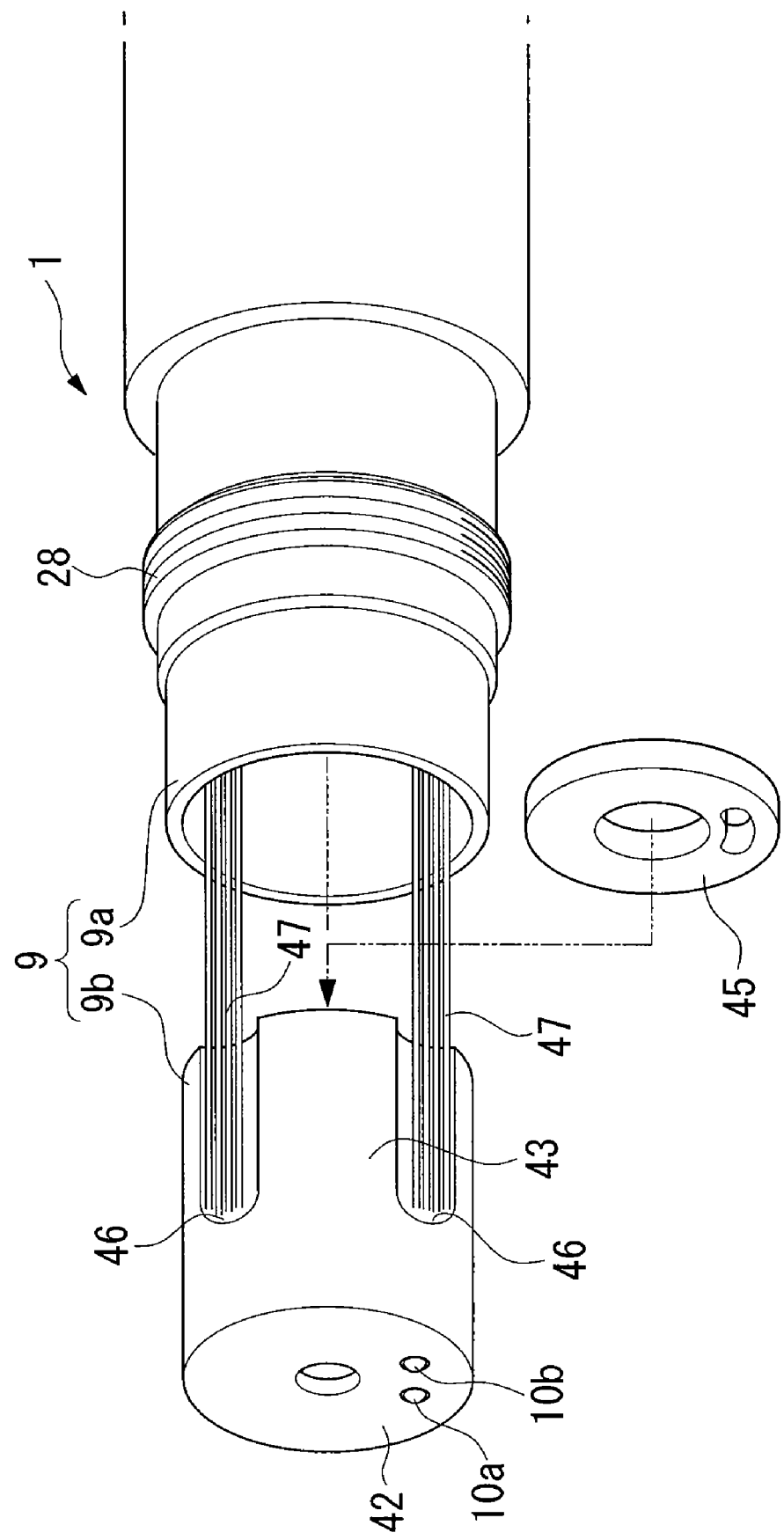
FIG. 7 is an exploded perspective view showing a distal end of an insertion portion provided in the endoscope device of the first embodiment.
Figure 8:
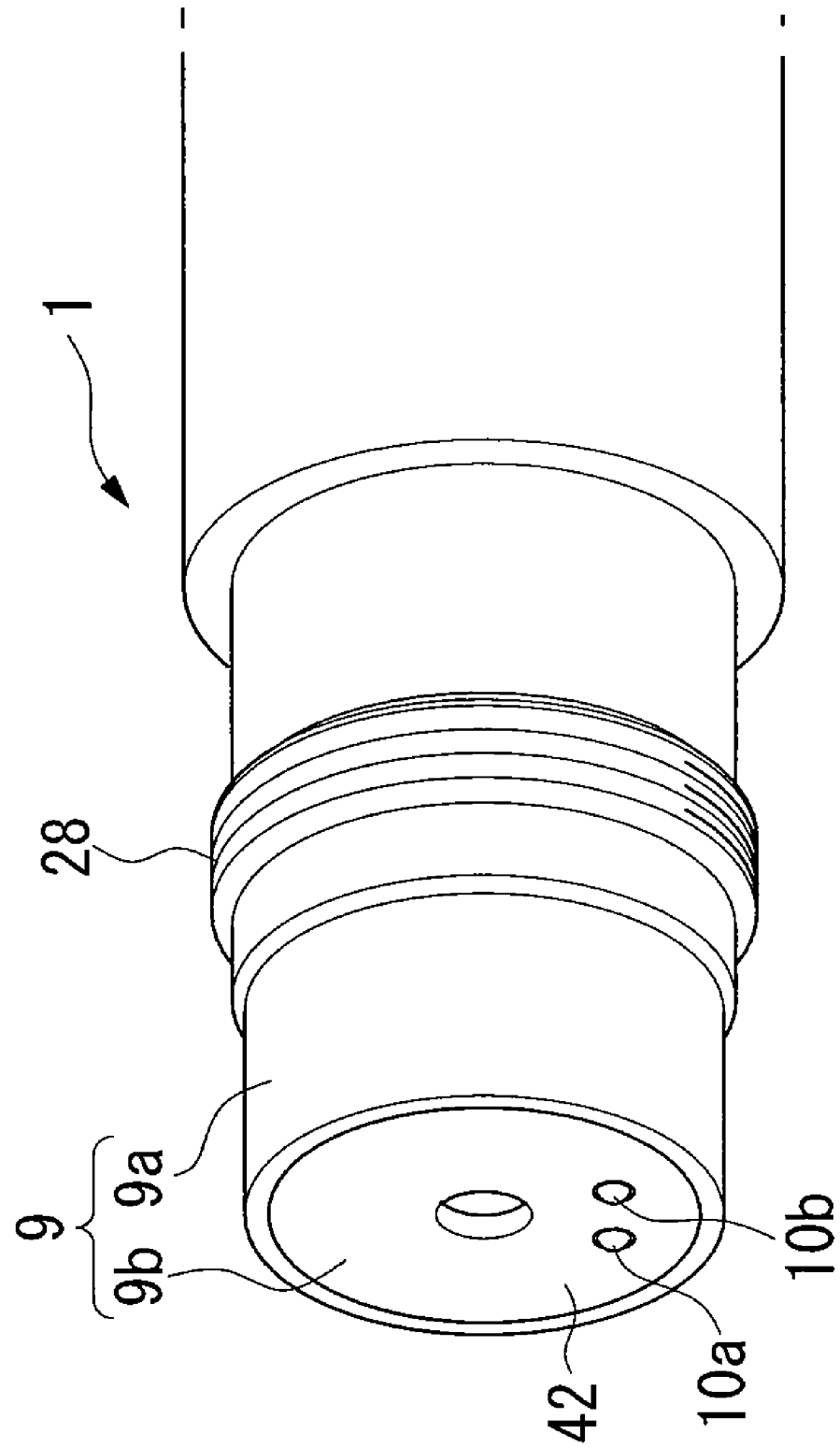
FIG. 8 is a perspective view showing a distal end of an insertion portion provided in the endoscope device of the first embodiment.

As is shown in FIG. 1 and FIG. 10, the above described CCD holder 9b of the connecting plug 9 is cut away in a toroidal shape from the rear surface side while leaving a front portion wall 42, an outer circumferential wall 43, and an inner circumferential wall 44 as they are. For example, a Peltier element sheet 45 is adhered as a circular plate-shaped cooling component onto a bottom surface of this toroidal recessed portion. This sheet 45 is a flexible sheet in which Peltier elements are embedded, and the side that is in close contact with the front portion wall 42 forms a cooling surface. Moreover, as is shown in FIG. 7, a plurality of hollowed out portions 46 having arc-shaped cross sections are formed extending in a longitudinal direction in the outer circumferential wall 43. Heat discharge wires (i.e., second heat discharging components) 47 that are formed from a highly thermoconductive metal such as copper are welded into the hollowed out portions 46. These heat discharge wires 47 are the same as the heat discharge wires 23 on the LED adaptor 2 side. The hollowed out portions 46 where the heat discharge wires 47 are fixed extend as far as a position adjacent to a bottom surface of the recessed portion. When the sheet 45 is attached to the bottom surface of the recessed portion, distal end portions of the heat discharge wires 47 are in contact with a heat discharge surface on the rear of the sheet 45 via an inner side curved area created in the hollowed out portions 46. The heat discharge wires 23 and 47 as well as the Peltier element sheet 45 constitute a heat removal portion that removes heat from components that are in contact therewith. Note that the symbol 48 in FIG. 1 and FIG. 10 shows wiring that supplies current to the Peltier element inside the sheet 45.

One end of the heat discharge wires 47 is connected to the CCD holder 9b, while, as is shown in FIG. 1 and FIG. 10, the other end of the heat discharge wires 47 is joined to a substantially cylindrical connecting component 49. The connecting component 49 is formed from a highly thermoconductive metal such as aluminum. An outer circumferential surface of the connecting component 49 fits together with the front connector 30 of the bending portion 3, and a front end portion of the internal coil 37 is joined to an inner circumferential surface of the connecting component 49.

In an endoscope device that is structured in the manner described above, heat generated by the LED chips 15 inside the LED adapter 2 is discharged to the outside in the manner described below. Note that, when the LED adapter 2 is connected to the distal end of the insertion portion 1 via the connecting ring 25, the rear surface of the lens supporting block 12 on the LED adapter 2 side is pressed so as to be in close contact with the front surface (i.e., with the front surface of the front portion wall 42 of the CCD holder 9b) of the connecting plug 9 on the insertion portion 1 side.

When the LED chips 15 are on continuously resulting in the LED chips 15 heating up, this heat is transmitted to the LED supporting block 13 located at the rear thereof. The heat is then further transmitted via the highly thermoconductive heat discharge wires 23 to the rear surface side of the lens supporting block 12. Because the rear end portions of the heat discharge wires 23 are in contact at the rear surface side of the lens supporting block 12 with the front surface of the CCD holder 9b located on the insertion portion 1 side, the heat that is transmitted to the rear end portion of the heat discharge wires 23 passes through this contact portion and is further transmitted to the CCD holder 9b.

At this time, in the CCD holder 9b, the Peltier element sheet 45 attached to the rear surface of the front portion wall 42 performs heat conversion so as to encourage heat to be transmitted from the front surface side of the front portion wall 42 towards the rear. As a result, the heat that is transmitted to the front portion wall 42 is discharged to the space behind the sheet 45, and is actively transmitted in the direction of the rear end of the outer circumferential wall 43 of the CCD holder 9b. In addition, the heat that is transmitted to the outer circumferential wall 43 is transmitted to the heat discharge wires 47, and is further transmitted from the heat discharge wires 47 via the connecting component 49 to the internal coil 37 of the bending portion 3. The heat that is transmitted to the internal coil 37 then escapes to the space on the base portion side of the elongated insertion portion 1.

Note that it is also possible to employ a different cooling component instead of the Peltier element 45. Examples thereof include highly thermoconductive metals such as copper and aluminum, ceramics such as aluminum nitride, and resins such as heat discharging silicon and heat discharging acrylic rubber sheets. In this case, heat is discharged to components in contact with a broader range of the front wall portion 42, thereby cooling the heat source.

As is described above, because this endoscope device makes it possible for heat generated by the LED chips 15 inside the LED adapter 2 to be transmitted efficiently to the connecting plug 9 at the distal end of the insertion portion 1 via the highly thermoconductive heat discharge wires 23, it is possible to prevent problems such as heat becoming concentrated inside the LED adaptor 2 and thereby causing a deterioration in the performance of the LED chips 15. Consequently, according to this endoscope device, it is possible to solve the problem of excessive LED heat and the insertion portion 1 and LED adapter 2 can be reduced in diameter.

Moreover, in the endoscope device of the present embodiment, because the heat discharge wires 47 are connected to the connecting plug 9 at the distal end of the insertion portion 1, and it is made easier for heat to be transmitted through the heat discharge wires 47 to the base portion side of the insertion portion 1, it is possible for the heat from the insertion portion 1 to be discharged efficiently to the outside over a wider range. In particular, in the present embodiment, because the Peltier element sheet 45 is attached to the interior of the CCD holder 9b of the connecting plug 9 and, utilizing the heat conversion effect of the sheet 45, heat transmission to the rear side of the insertion portion 1 is actively encouraged, more efficient heat discharge can be performed.

Moreover, in the present embodiment, because a structure is employed in the bending portion 3 that performs a bending operation by supplying air to or expelling air from the pressure chambers 33 of the columnar elastic component 34, heat that is transmitted to the connecting plug 9 can be easily blocked by the columnar elastic component 34. However, in this endoscope device, because end portions of the heat discharge wires 47 are connected via the connecting component 49 to the highly thermoconductive internal coil 37 inside the bending portion 3, it is possible, without the heat transmission by the columnar elastic component 34 being blocked, to reliably discharge heat over a broader area of the base portion side of the insertion portion 1.

Figure 11:
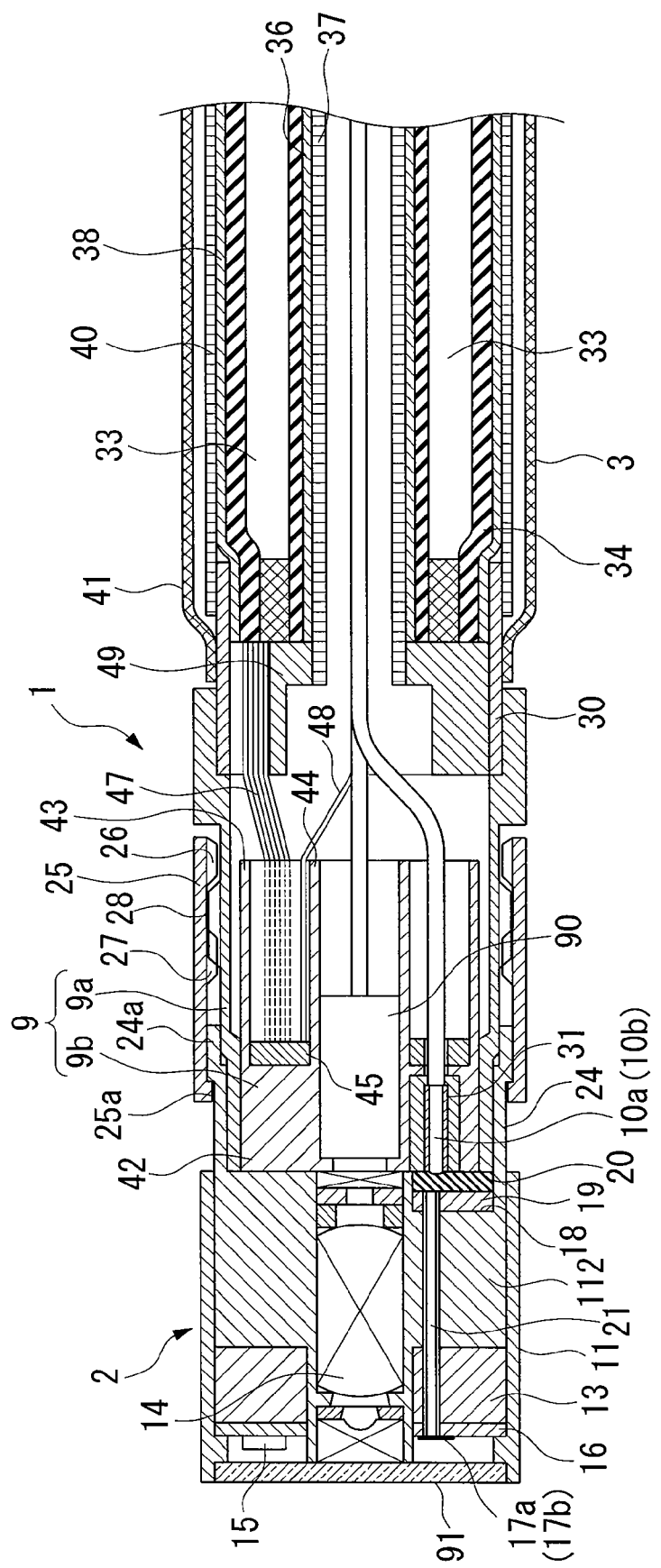
FIG. 11 is a longitudinal cross-sectional view showing a first variant example of the endoscope device of the first embodiment.

In the above described first embodiment, the through holes 22 are formed in the lens supporting block 12 and the heat discharge wires 23 are inserted through these through holes 22, however, as in a first variant example of the present embodiment shown in FIG. 11, it is also possible to provide a solid lens supporting block (i.e., thermoconductive component) 112 that does not have the through holes 22. The lens supporting block 112 is located on an inner side of the adapter housing 11 which is the exterior packaging component of the lens adapter 2. The LED supporting block 13 and the lens supporting block 112 are formed from a metal such as aluminum or copper, or from a ceramic material such as aluminum nitride, and the thermal conductivity thereof is higher than that of the stainless steel adapter housing 11.

Figure 12:
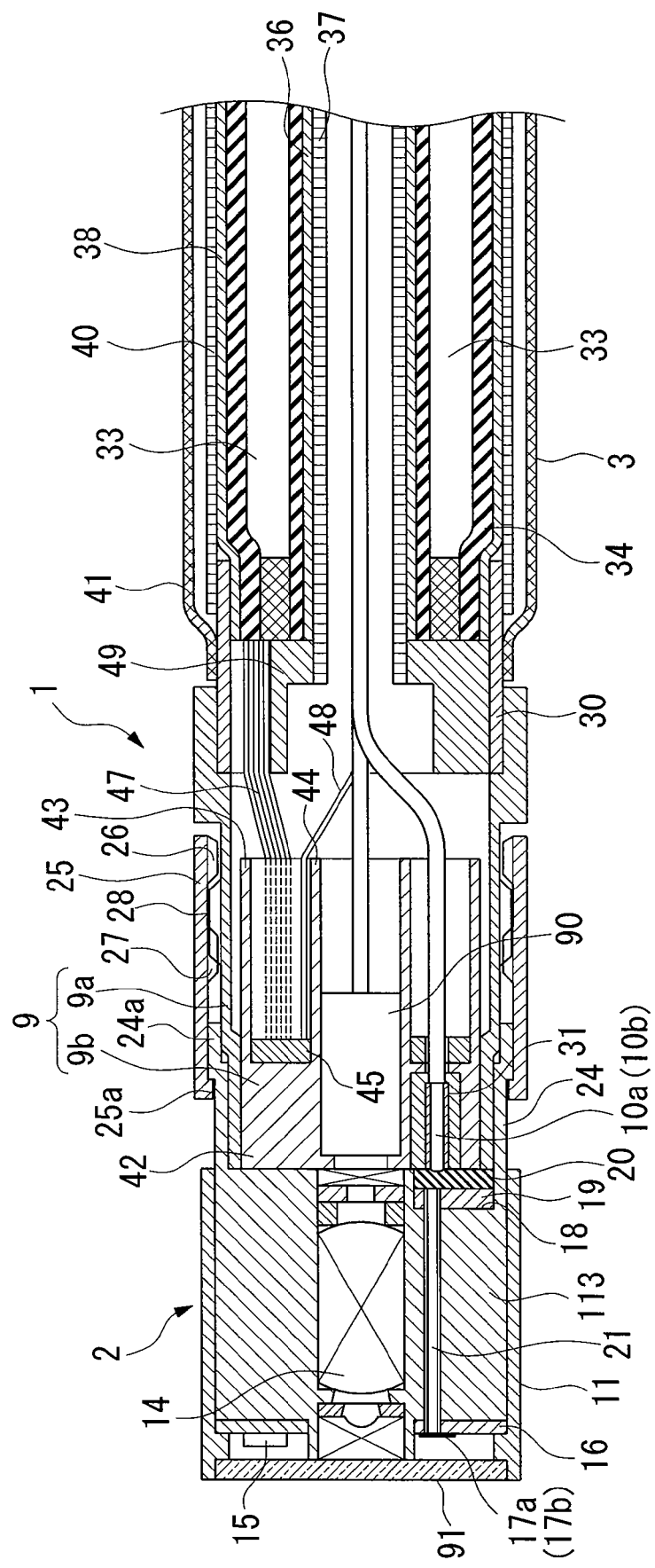
FIG. 12 is a longitudinal cross-sectional view showing a second variant example of the endoscope device of the first embodiment.

Moreover, as in a second variant example of the present embodiment shown in FIG. 12, it is also possible to form the LED supporting block 13 and the lens supporting block 112 as a single unit so as to provide an LED-lens supporting block (i.e., thermoconductive component) 113. The LED-lens supporting book 113 is formed from a metal such as aluminum or copper, or from a ceramic material such as aluminum nitride, and the thermal conductivity thereof is higher than that of the stainless steel adapter housing 11.

In each of the above described variant examples, heat generated by the LED chips 15 is not dissipated to the outside of the LED adapter 2, but is transmitted via the lens supporting block 12 or the LED-lens supporting book 113 to the front portion wall 42 of the insertion portion 1, and is discharged to the outside through the insertion portion 1.

Figure 13:
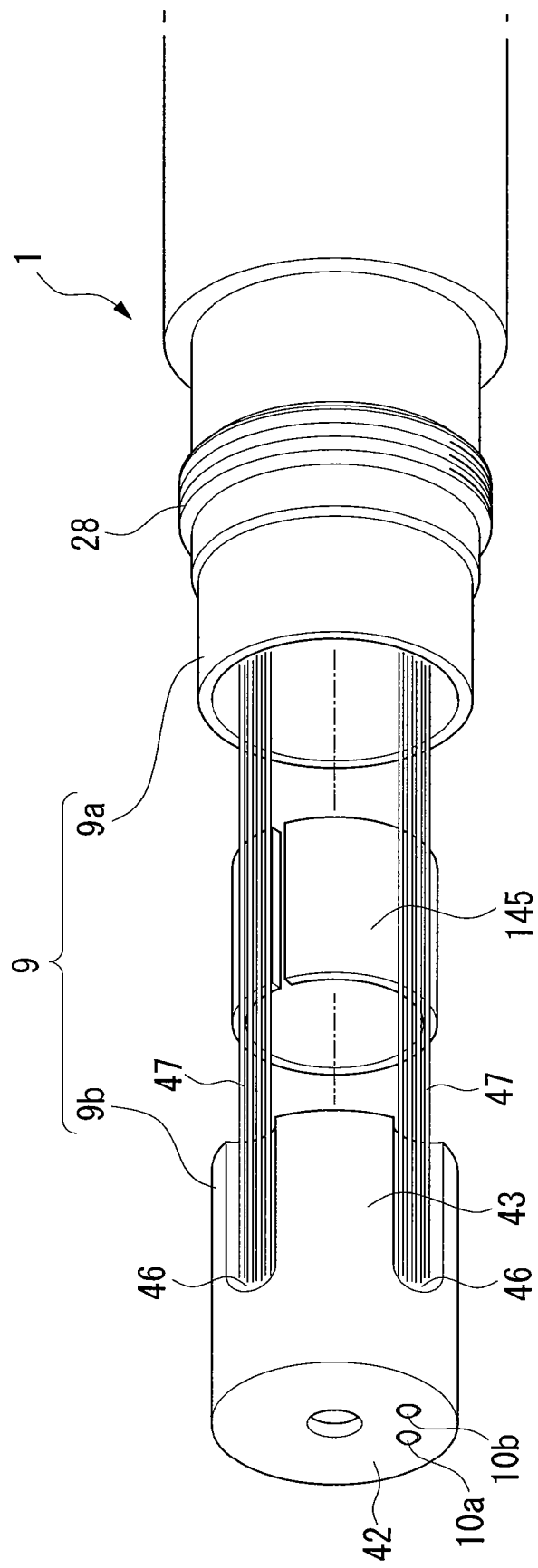
FIG. 13 is an exploded perspective view showing a distal end of an insertion portion provided in the endoscope device of a second embodiment of the present invention.
Figure 14:
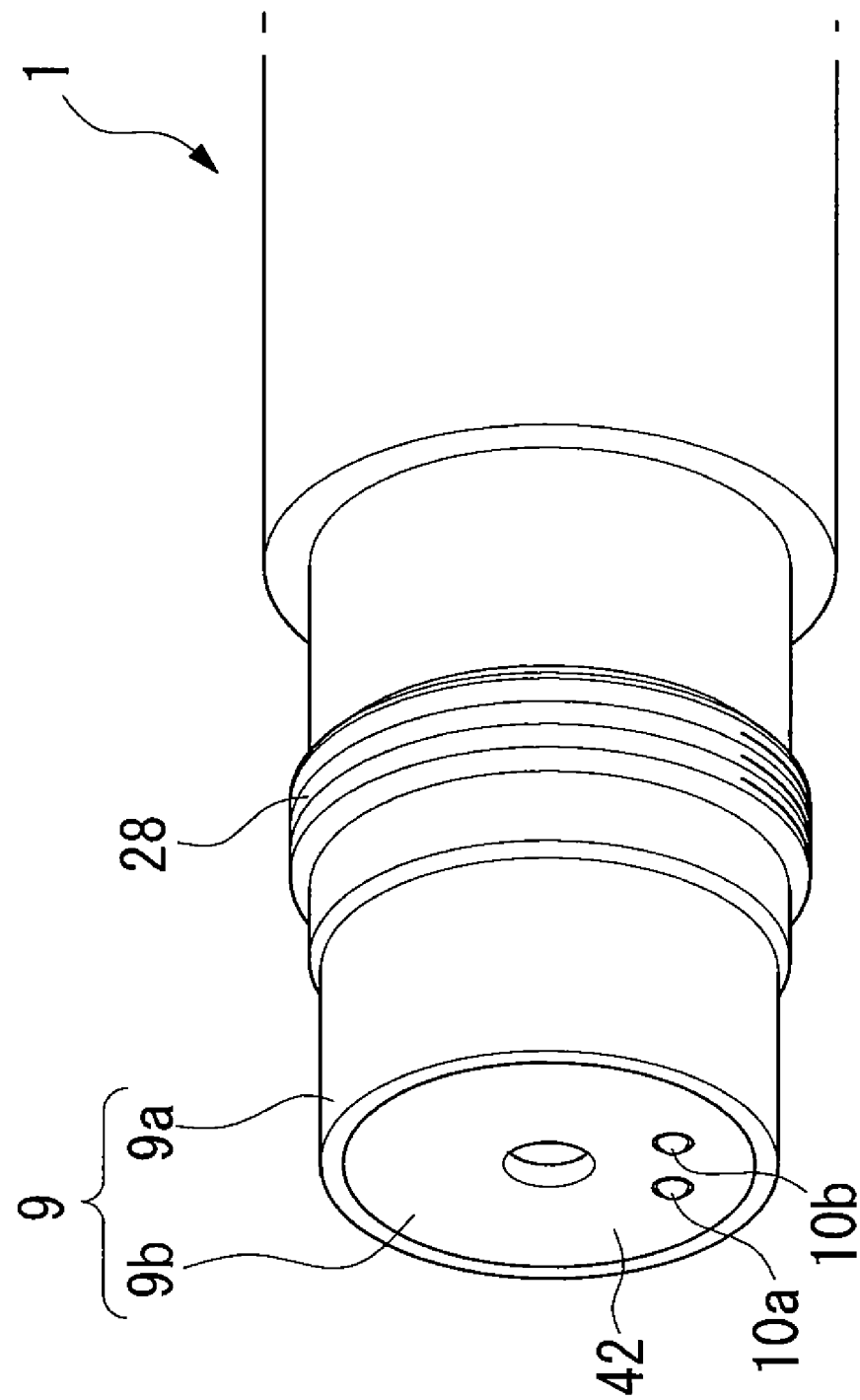
FIG. 14 is a perspective view showing a distal end of an insertion portion provided in the endoscope device of the second embodiment.

In the above described first embodiment, a circular plate-shaped Peltier element sheet 45 is attached to a rear surface of the front portion wall 42 of the CCD holder 9b, however, as in the second embodiment shown in FIG. 13 and FIG. 14, it is also possible to form a Peltier element sheet 145 in a rectangular shape, and transform this sheet 145 into a circular cylinder shape. The sheet 145 is then attached to the internal surface of the outer circumferential wall 43 of the CCD holder 9b such that a cooling surface thereof faces inwards in a radial direction. In this case, because heat transmission from the axial center portion of the CCD holder 9b towards the outer side in the radial direction is encouraged by the sheet 145, it is possible for heat that is transmitted from the LED adapter 2 to be efficiently transmitted to the heat discharge wires 47. Furthermore, heat that is generated by the CCD 90 in the axial center portion of the CCD holder 9b can also be reliably discharged towards the heat discharge wires 47 at the same time.

The description of other embodiments of the present invention is continued below.

Figure 15:
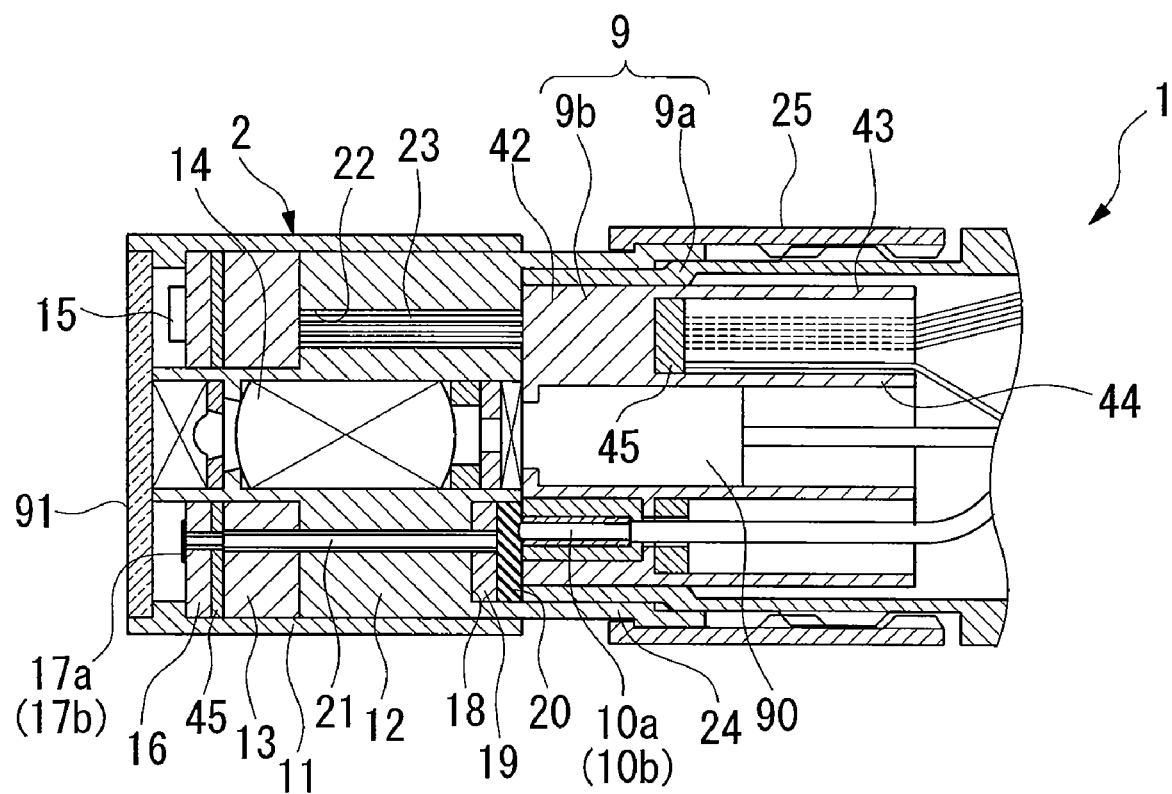
FIG. 15 is a longitudinal cross-sectional view showing principal portions of the endoscope device of a third embodiment of the present invention.

As is shown in FIG. 15, in the endoscope device of the third embodiment of the present invention, the Peltier element sheet 45 is inserted between the non-conductive plate-shaped component 16 inside the LED adaptor 2 and the LED supporting block 13. In addition, heat transmission from the LED chips 15 on the non-conductive plate-shaped component 16 to the LED supporting block 13 is encouraged by the heat conversion effect of the Peltier element sheet 45. Furthermore, the rear surface side of the LED chips 15 is actively cooled.

Figure 16:
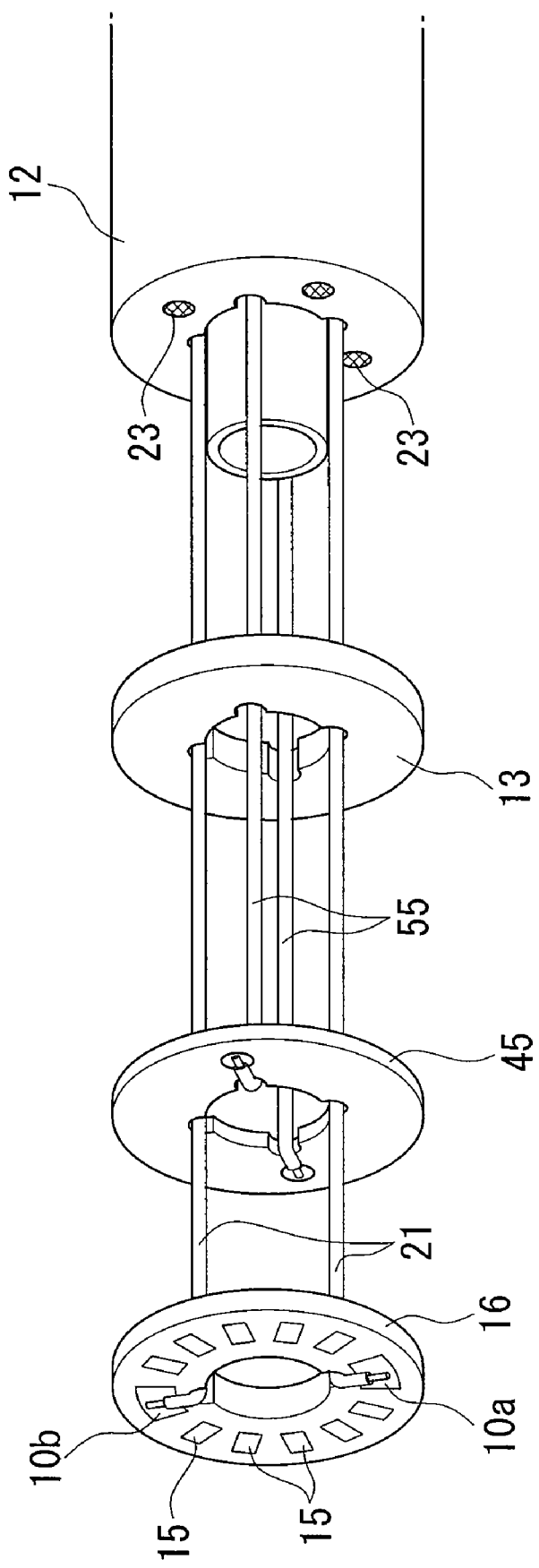
FIG. 16 is an exploded perspective view showing a first variant example of the endoscope device of the third embodiment.

Note that, in FIG. 15, the non-conductive plate-shaped component 16 is adhered to the Peltier element sheet 45, however, it is also possible for the two to be formed as a single unit and for a Peltier element to be embedded in a non-conductive plate-shaped component together with the LED chips 15 and the electrodes 10a and 10b and the like. Moreover, in FIG. 15, the wires for the Peltier element also function as the wires 21 for the LED chips 15, however, as in a first variant example of the present embodiment shown in FIG. 16, it is also possible for the wires 55 for the Peltier element and the wires 21 for the LED chips 15 to be provided separately.

Figure 17:
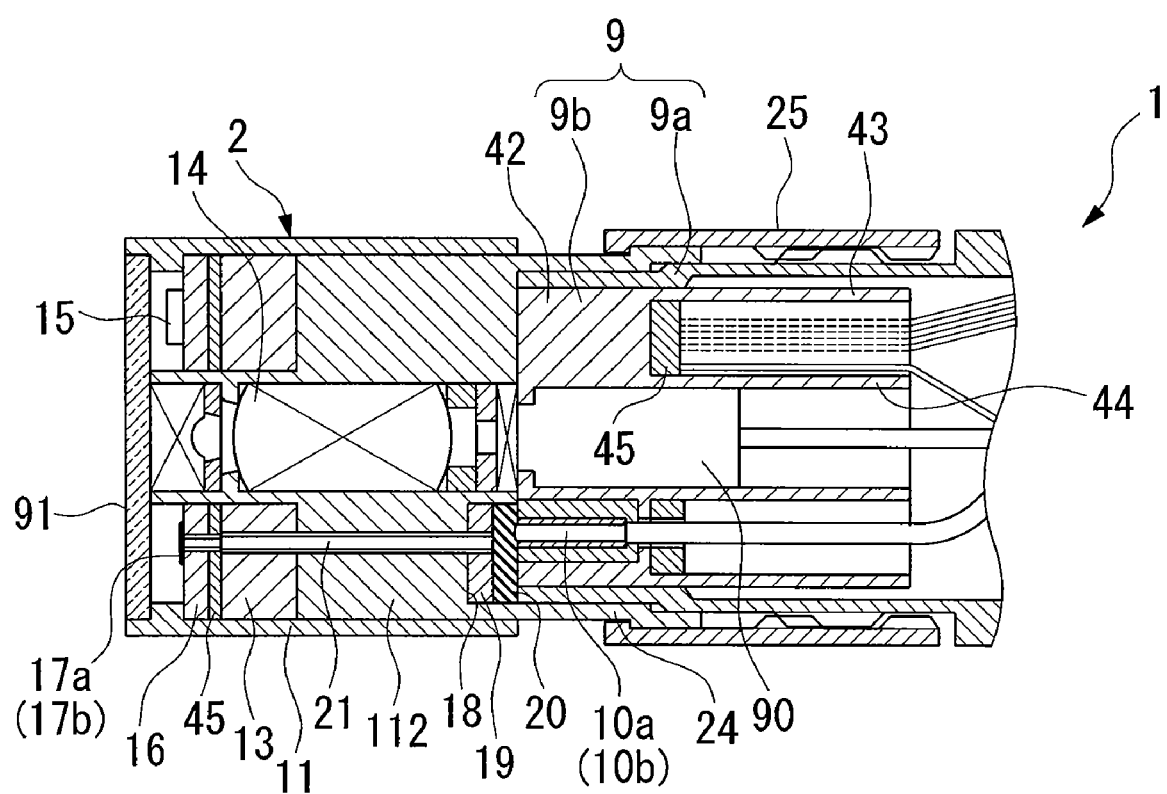
FIG. 17 is a longitudinal cross-sectional view showing a second variant example of the endoscope device of the third embodiment.

Moreover, as in a second variant example of the present embodiment shown in FIG. 17, it is also possible to provide a solid lens supporting block 112 that does not have the through holes 22. The lens supporting block 112 is located on an inner side of the adapter housing 11 which is the exterior packaging component of the lens adapter 2. The LED supporting block 13 and the lens supporting block 112 are formed from a metal such as aluminum or copper, or from a ceramic material such as aluminum nitride, and the thermal conductivity thereof is higher than that of the stainless steel adapter housing 11.

Figure 18:
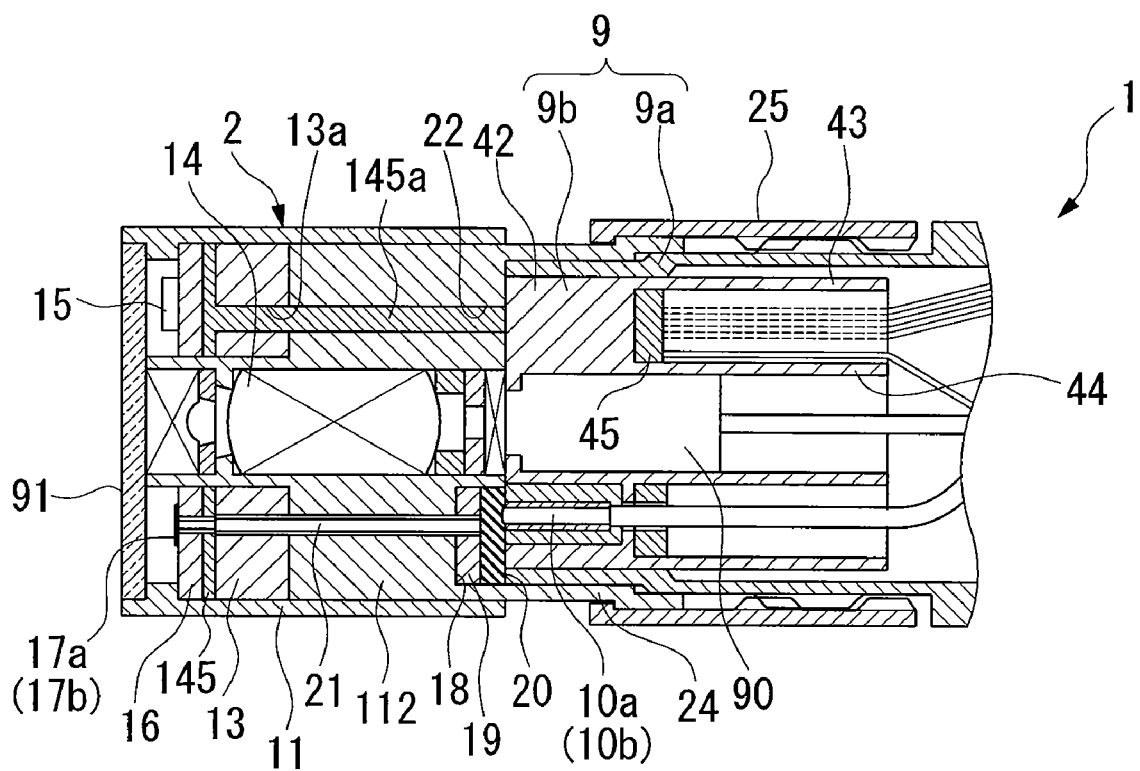
FIG. 18 is a longitudinal cross-sectional view showing a third variant example of the endoscope device of the third embodiment.

Moreover, as in a third variant example of the present embodiment shown in FIG. 18, a through hole 13a that communicates with the through hole 22 is formed in the LED supporting block 13. Furthermore, a thermoconductive component 145 is provided instead of the Peltier element sheet 45. A heat discharge portion 145a that is inserted into the through holes 22 and 13a is formed integrally with the thermoconductive component 145. A rear end surface of the heat discharge portion 145a is formed with substantially the same planar shape as the rear surface of the lens supporting block 12. When the LED adapter 2 is attached to the insertion portion 1, the rear end surface of the heat discharge portion 145a is in contact with the front portion wall 42 of the insertion portion 1. The thermoconductive component 145 is formed from a metal such as aluminum or copper, or from a ceramic material such as aluminum nitride. As a result, heat generated by the LED chips 15 is not dissipated to the outside of the LED adapter 2, but is transmitted mainly via the thermoconductive component 145 to the front portion wall 42 of the insertion portion 1, and is discharged to the outside through the insertion portion 1. Note that there may be one heat discharge portion 145a or a plurality of heat discharge portions 145a.

Figure 19:
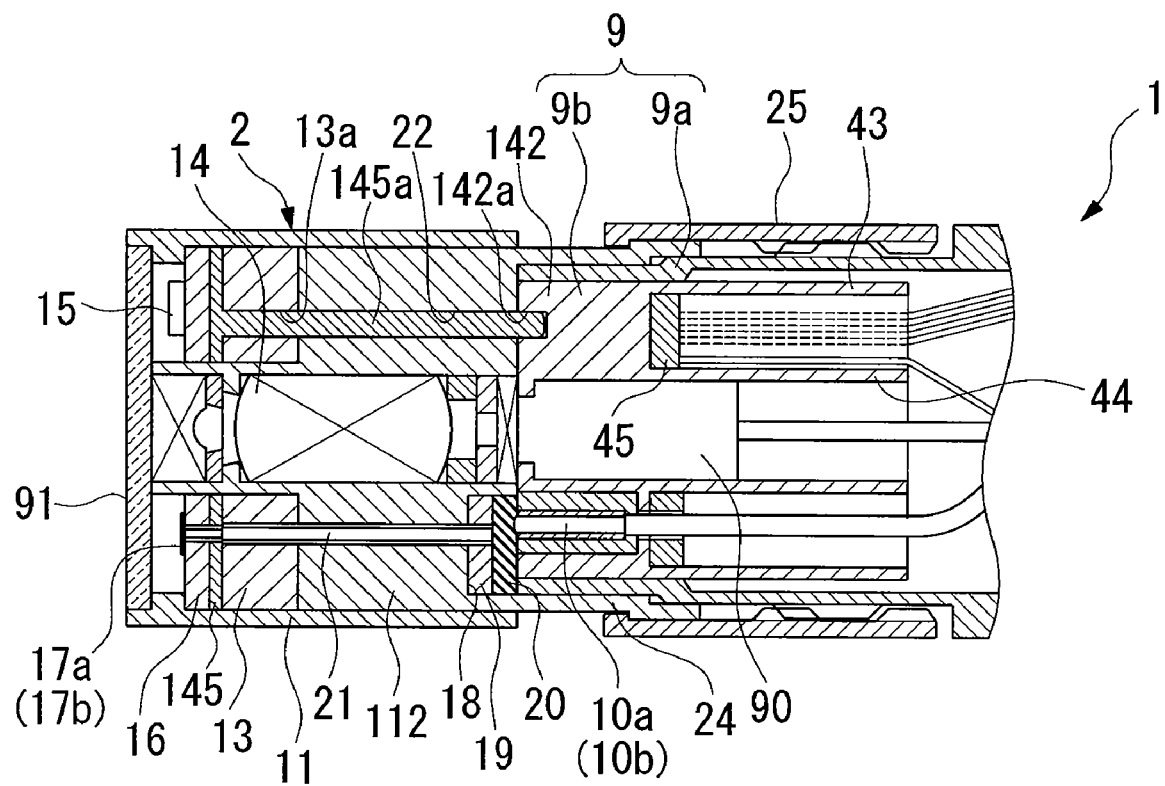
FIG. 19 is a longitudinal cross-sectional view showing a fourth variant example of the endoscope device of the third embodiment.

Moreover, as in the fourth variant example of the present embodiment shown in FIG. 19, a rear end of the heat discharge portion 145a of the thermoconductive component 145 is made to protrude from the rear surface of the lens supporting block 12. In contrast, a recessed portion 142a into which the rear end of the heat discharge portion 145a is inserted without any gaps when the LED adapter 2 is mounted is formed in the front portion wall 142 of the insertion portion 1. By inserting the rear end of the heat discharge portion 145a in the recessed portion 142a, it becomes easy for heat to be exchanged between the heat discharge portion 145a and the connecting plug 9. As a result, heat generated by the LED chips 15 is efficiently transmitted to the front portion wall 42 of the insertion portion 1.

Figure 20:
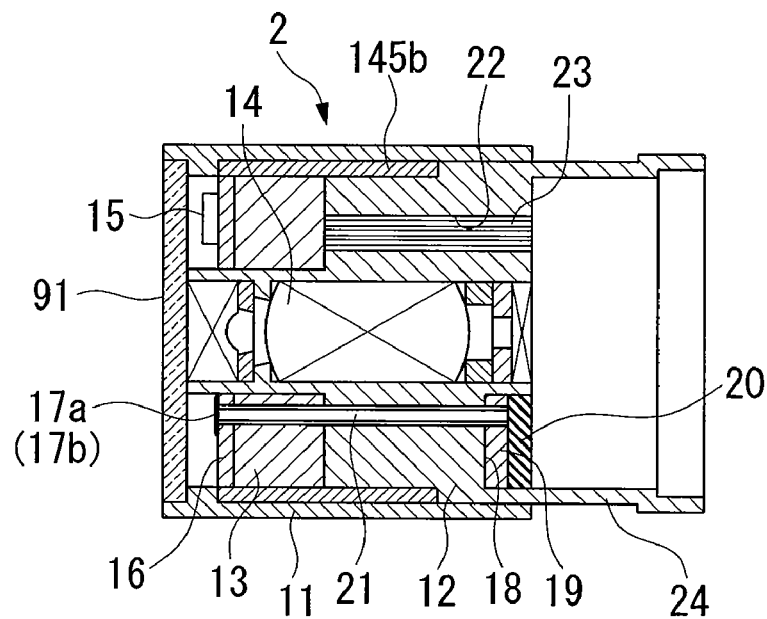
FIG. 20 is a longitudinal cross-sectional view showing principal portions of an endoscope device of a fourth embodiment of the present invention.

In the fourth embodiment shown in FIG. 20, a Peltier element sheet 145b is attached to the outer circumferential surface of the LED supporting block 13 and the lens supporting block 12. Heat transmission from the two blocks 13 and 12 to the adapter housing 11 is encouraged by the Peltier element sheet 145b.

Figure 21:
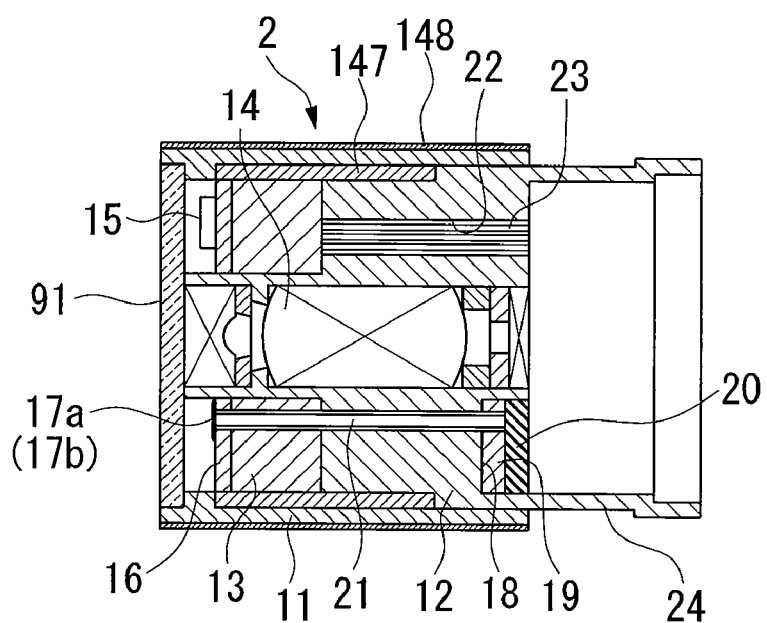
FIG. 21 is a longitudinal cross-sectional view showing a first variant example of the endoscope device of the fourth embodiment.

As in the first variant example of the present embodiment shown in FIG. 21, a thermoconductive component 147 having the same shape as the Peltier element sheet 45 is provided instead of the Peltier element sheet 45. As a result of being inserted between the lens supporting block 12 and LED supporting block 13 and the adapter housing 11, the thermoconductive component 147 is placed tightly against the lens supporting block 12 and the LED supporting block 13. The thermoconductive component 147 is formed from a resin material such as conductive rubber, silicon rubber, or acrylic rubber. The adapter housing 11 is formed from a metal such as aluminum, and a protective layer 148 is formed on the surface thereof by hard alumite processing or the like. The protective layer 148 protects the surface of the aluminum adapter housing 11 which is easily scratched and easily gouged.

Heat generated by the LED chips 15 is dissipated radially to the area surrounding the LED adapter 2 via the LED supporting block 13 and the thermoconductive component 147.

Note that, instead of the above described resin materials, the thermoconductive component 147 may be a soft, highly thermoconductive metal such as copper, and this thermoconductive component 147 may be pushed under pressure between the lens supporting block 12 and LED supporting block 13 and the adapter housing 11 so that the shape thereof is transformed.

Figure 22:
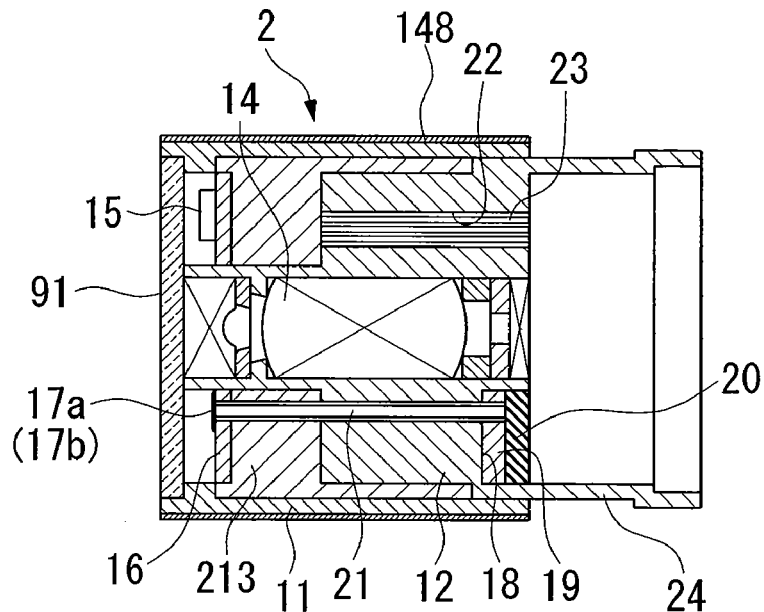
FIG. 22 is a longitudinal cross-sectional view showing a second variant example of the endoscope device of the fourth embodiment.

Moreover, as in the second variant example of the present embodiment shown in FIG. 22, instead of the LED supporting block 13 and the thermoconductive component 147, a thermoconductive component 213 may be provided by integrating these two into a single unit. The thermoconductive component 213 is formed from a metal such as aluminum or copper, or from a ceramic material such as aluminum nitride.

Heat generated by the LED chips 15 is dissipated radially to the area surrounding the LED adapter 2 via the thermoconductive component 213.

Figure 23:
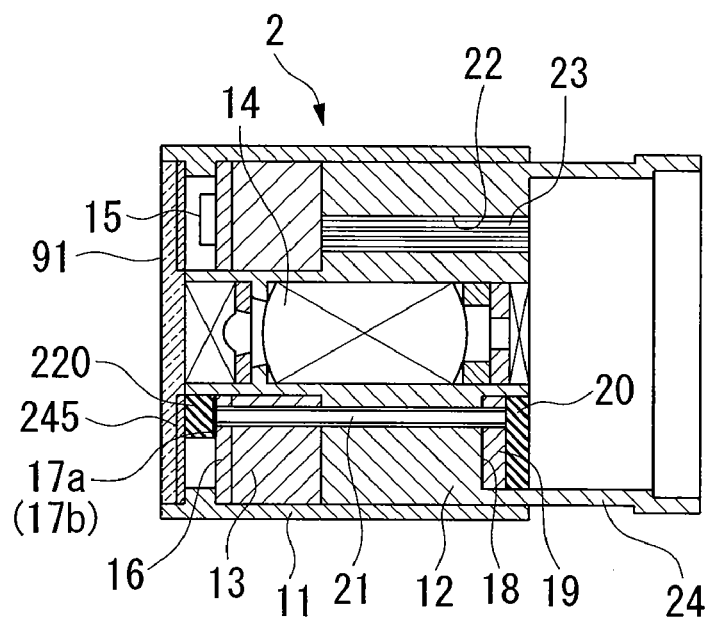
FIG. 23 is a longitudinal cross-sectional view showing principal portions of the endoscope device of a fifth embodiment of the present invention.

In the fifth embodiment shown in FIG. 23, a Peltier element sheet 245 is formed using a transparent resin material as a base, and heat discharge from a front surface of the sealing glass 91 is encouraged by adhering this sheet 245 to a rear surface of the sealing glass 91. In this case, power is supplied to the Peltier element via conductive rubber 220 (that has the same functions and structure as the above described conductive rubber 20) that is placed at front surfaces of the electrodes 10a and 10b for the LED chips 15.

Figure 24:
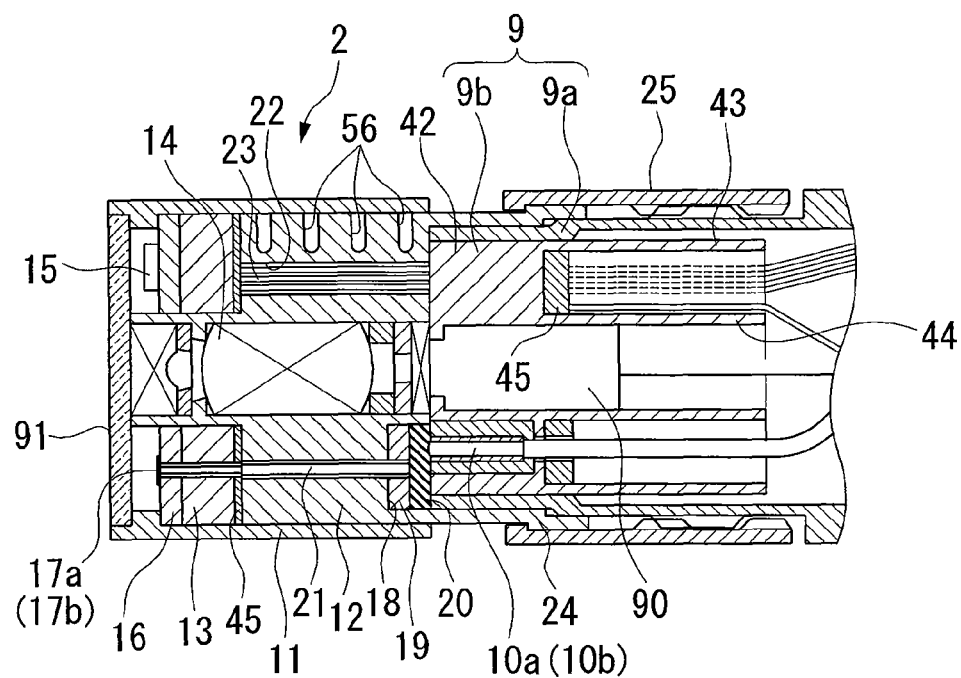
FIG. 24 is a longitudinal cross-sectional view showing principal portions of the endoscope device of a sixth embodiment of the present invention.

In the sixth embodiment shown in FIG. 24, the Peltier element sheet 45 is interposed between the LED supporting block 13 and the lens supporting block 12, and front end portions of the heat discharge wires 23 are connected to the rear surface of the LED supporting block 13 via the sheet 45. In this case, heat transmission from the LED supporting block 13 to the heat discharge wires 23 is encouraged by the heat exchange action of the Peltier element sheet 45, and heat discharge via the lens supporting block 12 to the outer circumferential side of the LED adapter 2 is encouraged.

Moreover, in the present embodiment, the heat discharge performance of the lens supporting block 12 is improved as a result of a plurality of grooves 56 being formed in the outer circumferential surface of the lens supporting block 12.

Figure 25:
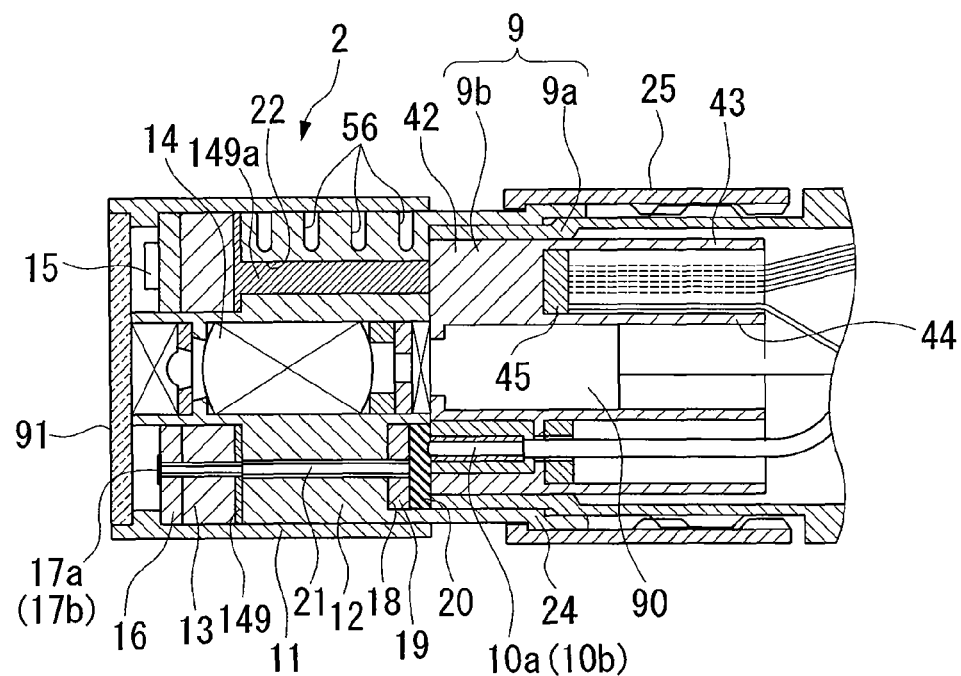
FIG. 25 is a longitudinal cross-sectional view showing a first variant example of the endoscope device of the sixth embodiment.

As in the first variant example of the present embodiment shown in FIG. 25, a thermoconductive component 149 having the same shape as the Peltier element sheet 45 is provided instead of the Peltier element sheet 45. A heat discharge portion 149a that is inserted into the through hole 22 is provided integrally with the thermoconductive component 149. A rear end surface of the heat discharge portion 149a is formed with substantially the same planar shape as the rear surface of the lens supporting block 12. When the LED adapter 2 is attached to the insertion portion 1, the rear end surface of the heat discharge portion 149a is in contact with the front portion wall 42 of the insertion portion 1. The thermoconductive component 149 is formed from a metal such as aluminum or copper, or from a ceramic material such as aluminum nitride.

Figure 26:
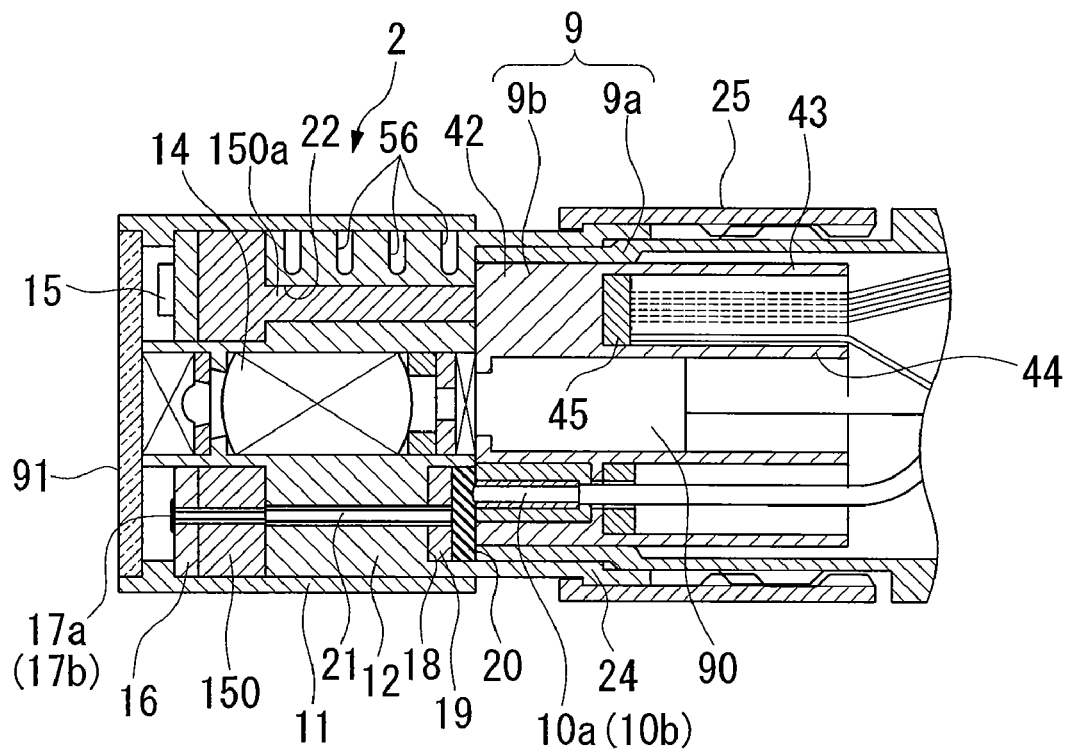
FIG. 26 is a longitudinal cross-sectional view showing a second variant example of the endoscope device of the sixth embodiment.

Moreover, as in the second variant example of the present embodiment shown in FIG. 26, instead of the LED supporting block 13 and the Peltier element sheet 45, a thermoconductive component 150 may be provided by integrating these two into a single unit. A heat discharge portion 150a that is inserted into the through holes 22 is formed integrally with the thermoconductive component 150. A rear end surface of the heat discharge portion 150a is formed with substantially the same planar shape as the rear surface of the lens supporting block 12. When the LED adapter 2 is attached to the insertion portion 1, the rear end surface of the heat discharge portion 150a is in contact with the front portion wall 42 of the insertion portion 1. The thermoconductive component 150 is formed from a metal such as aluminum or copper, or from a ceramic material such as aluminum nitride.

In each of the above described variant examples, heat generated by the LED chips 15 is not dissipated to the outside of the LED adapter 2, but is transmitted mainly via the thermoconductive component 149 or the thermoconductive component 150 to the front portion wall 42 of the insertion portion 1, and is discharged to the outside through the insertion portion 1.

Figure 27:
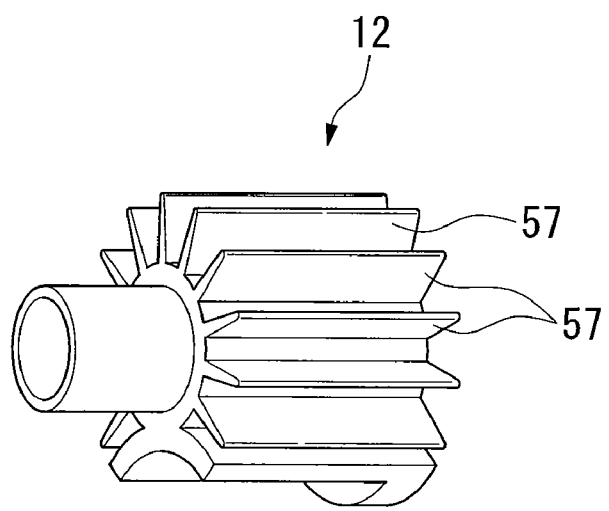
FIG. 27 is perspective view showing a variant example of a lens supporting block that is provided in the endoscope device of the sixth embodiment.

As in the variant example of the present embodiment shown in FIG. 27, it is also possible for a plurality of fins 57 to be formed extending in an axial direction on the outer circumferential side of the lens supporting block 12, so that the heat discharge performance of the lens supporting block 12 is improved by this fin structure.

Figure 28:
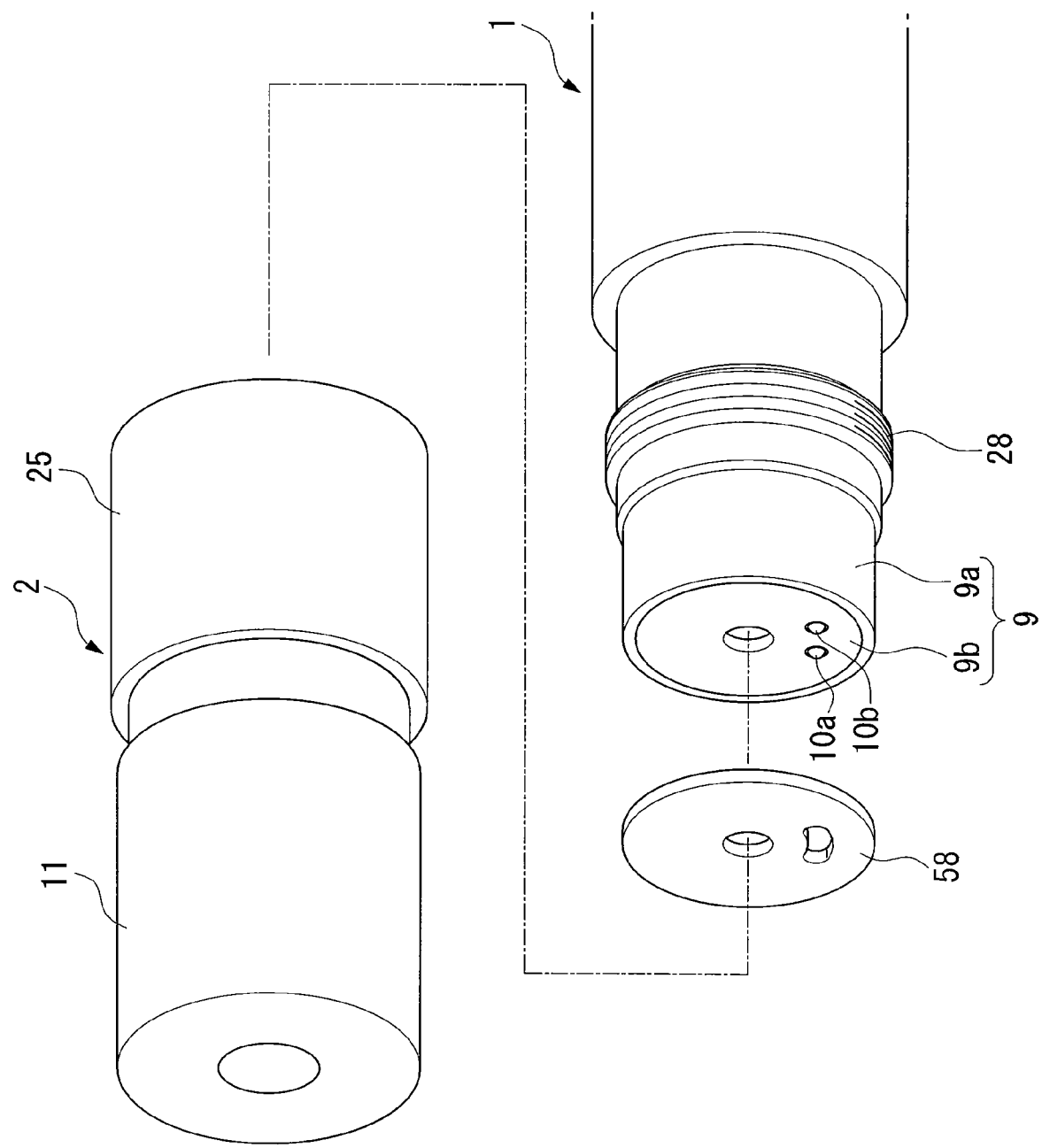
FIG. 28 is an exploded perspective view showing the endoscope device of a seventh embodiment of the present invention.

FIG. 28 shows the seventh embodiment of the present invention. In the present embodiment, a thermoconductive sheet 58 that is formed from a highly thermoconductive elastic material such as silicon is attached to a front surface of the connecting plug 9 at the distal end of the insertion portion 1, so that the level of adhesion between the rear surface of the LED adapter 2 and the distal end of the insertion portion 1 is increased. If the level of adhesion between the rear surface of the LED adapter 2 and the distal end of the insertion portion 1 is increased in this manner, heat is more reliably transmitted to the insertion portion 1 side through the heat discharge wires 23 on the LED adapter 2 side.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as limited by the foregoing description and is only limited by the scope of the appended claims.

The endoscope device of the present invention includes: an LED adaptor that has a plurality of LED chips and that can be removably fitted onto a distal end of an insertion portion that is inserted into a body cavity of an endoscopy subject; an LED supporting block that is provided on the LED adaptor and that supports the plurality of LED chips; and a heat removal portion that removes heat from the LED supporting block.

According to the present invention, heat that is generated by the LED chips inside the LED adaptor can be efficiently transmitted to the distal end portion of the insertion portion via the LED supporting block and the heat removal portion. Accordingly, it is possible to prevent heat becoming concentrated in peripheral portions of the LED chips and reliably prevent any deterioration in the performance of the LED chips that is caused by heat.

In the endoscope device of the present invention, it is also possible for the heat removal portion to transmit the heat from the LED supporting block to another place, and it is also possible for the heat removal portion to cool the LED supporting block.

According to the present invention, heat that is generated by the LED chips is manly transmitted to the LED supporting block. The heat that is transmitted to the LED supporting block is transmitted by the heat removal portion to another place or is cooled by the heat removal portion.

In the endoscope device of the present invention, it is also possible for the heat removal portion to be provided with a first heat discharge component that has one end that is connected to the LED supporting block and has another end that extends as far as a rear end surface of the LED adaptor, and when the LED adaptor is mounted on the insertion portion, for the other end of the first heat discharge component to be in contact with a distal end surface of the insertion portion.

According to the present invention, heat that is generated by the LED chips is transmitted to the distal end surface of the insertion portion mainly via the LED supporting block and the first heat discharge wires, and is discharged to the outside through the insertion portion.

In the endoscope device of the present invention, it is also possible for the heat removal portion to be provided with: a connecting plug that is provided at the distal end of the insertion portion and is in contact with the first heat discharge component: and with a second heat discharge component that is provided inside the insertion portion and that has one end that is connected to the connecting plug and has another end that extends to a proximal end side of the insertion portion, and when the LED adaptor is mounted on the insertion portion, for the other end of the first heat discharge component to be in contact with the connecting plug.

According to the present invention, heat that is transmitted to the connecting plug via the first heat discharge wires is transmitted to the proximal end side of the insertion portion via the second heat discharge wires. Accordingly, because heat no longer accumulates in one place but is discharged over a wide range, the heat discharge efficiency is further improved.

In the endoscope device of the present invention, it is also possible for the heat removal portion to be further provided with a heat transmitting portion that is provided between the connecting plug and the second heat discharge component.

According to the present invention, it is possible to transmit heat reliably from the connecting plug to the second heat discharge wires using the action of the heat transmitting portion. As a result, the heat discharge effect inside the insertion portion is further improved.

In the endoscope device of the present invention, it is also possible for the heat removal portion to be further provided with a heat transmitting portion that is provided on an outer circumferential surface of the LED adaptor.

According to the present invention, heat that is peripheral to the axial center portion of the LED adaptor is easily transmitted towards the outer side in the radial direction of the LED adaptor, and it becomes easier for heat to be transmitted to the second heat discharge wires and outer circumferential surface of the LED adaptor.

In the endoscope device of the present invention, it is also possible for the heat removal portion to be further provided with a heat transmitting portion that is provided between the LED chips and the LED supporting block, or between the LED supporting block and the first heat discharge component.

According to the present invention, the transmission of heat within the LED adaptor is further accelerated by the action of the heat transmitting portion.

In the endoscope device of the present invention, it is also possible for the heat removal portion to be further provided with a heat transmitting portion that is provided on an outer circumferential surface of the LED supporting block.

According to the present invention, the transmission of heat towards the outer side of the LED adaptor is accelerated by the action of the heat transmitting portion.

In the endoscope device of the present invention, it is also possible for the heat transmitting portion to be a Peltier element.

According to the present invention, because heat is actively transmitted as a result of the heat conversion effect of the Peltier element in a direction in which the heat from the LED is expelled, the heat discharge effect in the respective portions where the Peltier element is provided is considerably improved.

In the endoscope device of the present invention, it is also possible for a bending portion that is able to perform a bending operation in an optional direction to be provided in the distal end portion, and for the bending portion to be formed by a columnar elastic component having a plurality of pressure chambers that are aligned in a circumferential direction, and for the bending portion to perform a bending operation as a result of highly pressurized air being selectively supplied to or discharged from the plurality of pressure chambers of the columnar elastic material, and for the columnar elastic component to be formed in a circular cylinder shape, and for a highly thermoconductive internal coil that regulates displacement towards an inner side in a radial direction to be placed on an inner circumferential side of the columnar elastic component that is formed in a circular cylinder shape, and for the other end of the second heat discharge component to be connected to the internal coil.

According to the present invention, it is possible for heat that is transmitted from the LED adaptor side to the insertion portion to be discharged towards the rear side of the bending portion via the second heat discharge wires and the highly thermoconductive internal coil. According, the heat discharge area within the insertion portion is widened and the heat discharge performance is further improved.

In the endoscope device of the present invention, it is also possible for the LED adaptor to be provided with: an exterior packaging component; and a thermoconductive component that is provided on an inner side of the exterior packaging component and is more highly thermoconductive than the exterior packaging portion. It is also possible for the thermoconductive component to be in contact with the LED chips and the distal end surface of the insertion portion.

In the endoscope device of the present invention, it is also possible for the thermoconductive component to have either a linear shape, a block shape, or a cylindrical shape. It is also possible for the thermoconductive component to be formed from any one of a metal such as aluminum or copper, a ceramic such as aluminum nitride, or a resin such as silicon rubber or acrylic rubber.

According to the present invention, because a thermoconductive component is provided that is more highly thermoconductive than the exterior packaging of the LED adaptor, heat generated by the LED chips is not dissipated to the outside of the LED adaptor, but is transmitted to the distal end surface of the insertion portion manly via the thermoconductive component, and is discharged to the outside through the insertion portion.

The endoscope device of the present invention is favorable for use in medicine and industry.

What is claimed is:

1. An endoscope device comprising:
    an LED adaptor that has a plurality of LED chips and that can be removably fitted onto a distal end of an insertion portion that is inserted into a body cavity of an endoscopy subject;
    an LED supporting block that is provided on the LED adaptor and that supports the plurality of LED chips; and
    a heat removal portion that removes heat from the LED supporting block, wherein the heat removal portion is provided with a first heat discharge component that has one end that is connected to the LED supporting block and has another end that extends as far as a rear end surface of the LED adaptor,
    when the LED adaptor is mounted on the insertion portion, the other end of the first heat discharge component is in contact with a distal end surface of the insertion portion,
    the heat removal portion is provided with: a connecting plug that is provided at the distal end of the insertion portion and is in contact with the first heat discharge component:
    a second heat discharge component that is provided inside the insertion portion and that has one end that is connected to the connecting plug and has another end that extends to a proximal end side of the insertion portion,
    when the LED adaptor is mounted on the insertion portion, the other end of the first heat discharge component is in contact with the connecting plug,
    the heat removal portion is further provided with a heat transmitting portion that is provided between the connecting plug and the second heat discharge component, and
    the heat transmitting portion is a Peltier element.

2. The endoscope device according to claim 1, wherein the heat removal portion transmits the heat from the LED supporting block to another place.

3. The endoscope device according to claim 1, wherein the heat removal portion cools the LED supporting block.

4. The endoscope device according to claim 1, wherein
    a bending portion that is able to perform a bending operation in an optional direction is provided in the distal end portion,
    the bending portion is formed by a columnar elastic component having a plurality of pressure chambers that are aligned in a circumferential direction, and the bending portion performs a bending operation as a result of highly pressurized air being selectively supplied to or discharged from the plurality of pressure chambers of the columnar elastic material,
    the columnar elastic component is formed in a circular cylinder shape,
    a highly thermoconductive internal coil that regulates displacement towards an inner side in a radial direction is placed on an inner circumferential side of the columnar elastic component that is formed in a circular cylinder shape, and
    the other end of the second heat discharge component is connected to the internal coil.

5. An endoscope device comprising:
    an LED adaptor that has a plurality of LED chips and that can be removably fitted onto a distal end of an insertion portion that is inserted into a body cavity of an endoscopy subject;
    an LED supporting block that is provided on the LED adaptor and that supports the plurality of LED chips; and
    a heat removal portion that removes heat from the LED supporting block, wherein
    the heat removal portion is provided with a first heat discharge component that has one end that is connected to the LED supporting block and has another end that extends as far as a rear end surface of the LED adaptor,
    when the LED adaptor is mounted on the insertion portion, the other end of the first heat discharge component is in contact with a distal end surface of the insertion portion,
    the heat removal portion is provided with: a connecting plug that is provided at the distal end of the insertion portion and is in contact with the first heat discharge component:
    a second heat discharge component that is provided inside the insertion portion and that has one end that is connected to the connecting plug and has another end that extends to a proximal end side of the insertion portion,
    when the LED adaptor is mounted on the insertion portion, the other end of the first heat discharge component is in contact with the connecting plug,
    the heat removal portion is further provided with a heat transmitting portion that is provided between the LED chips and the LED supporting block, and
    the heat transmitting portion is a Peltier element.

6. An endoscope device comprising:
    an LED adaptor that has a plurality of LED chips and that can be removably fitted onto a distal end of an insertion portion that is inserted into a body cavity of an endoscopy subject;
    an LED supporting block that is provided on the LED adaptor and that supports the plurality of LED chips; and
    a heat removal portion that removes heat from the LED supporting block, wherein
    the heat removal portion is provided with a first heat discharge component that has one end that is connected to the LED supporting block and has another end that extends as far as a rear end surface of the LED adaptor,
    when the LED adaptor is mounted on the insertion portion, the other end of the first heat discharge component is in contact with a distal end surface of the insertion portion,
    the heat removal portion is provided with: a connecting plug that is provided at the distal end of the insertion portion and is in contact with the first heat discharge component:
    a second heat discharge component that is provided inside the insertion portion and that has one end that is connected to the connecting plug and has another end that extends to a proximal end side of the insertion portion, when the LED adaptor is mounted on the insertion portion, the other end of the first heat discharge component is in contact with the connecting plug, the heat removal portion is further provided with a heat transmitting portion that is provided between the LED supporting block and the first heat discharge component, and the heat transmitting portion is a Peltier element.

7. An endoscope device comprising:

an LED adaptor that has a plurality of LED chips and that can be removably fitted onto a distal end of an insertion portion that is inserted into a body cavity of an endoscopy subject;

an LED supporting block that is provided on the LED adaptor and that supports the plurality of LED chips; and a heat removal portion that removes heat from the LED supporting block, wherein the heat removal portion is provided with a first heat discharge component that has one end that is connected to the LED supporting block and has another end that extends as far as a rear end surface of the LED adaptor, when the LED adaptor is mounted on the insertion portion, the other end of the first heat discharge component is in contact with a distal end surface of the insertion portion, the heat removal portion is provided with: a connecting plug that is provided at the distal end of the insertion portion and is in contact with the first heat discharge component:

a second heat discharge component that is provided inside the insertion portion and that has one end that is connected to the connecting plug and has another end that extends to a proximal end side of the insertion portion, when the LED adaptor is mounted on the insertion portion, the other end of the first heat discharge component is in contact with the connecting plug, the heat removal portion is further provided with a heat transmitting portion that is provided on an outer circumferential surface of the LED supporting block, and the heat transmitting portion is a Peltier element.

8. An endoscope device comprising:

an LED adaptor that has a plurality of LED chips and that can be removably fitted onto a distal end of an insertion portion that is inserted into a body cavity of an endoscopy subject;

an LED supporting block that is provided on the LED adaptor and that supports the plurality of LED chips; and a heat removal portion that removes heat from the LED supporting block, wherein the LED adaptor is provided with: an exterior packaging component;

a thermoconductive component that is provided on an inner side of the exterior packaging component and is more highly thermoconductive than the exterior packaging portion, and the thermoconductive component is in contact with the LED chips and the distal end surface of the insertion portion.

9. The endoscope device according to claim 8, wherein the thermoconductive component has either a linear shape, a block shape, or a cylindrical shape.

10. The endoscope device according to claim 8, wherein the thermoconductive component is formed from either metal, ceramic, or resin.

* * * * *